US011633208B2

(12) United States Patent
Molinaro et al.

(10) Patent No.: US 11,633,208 B2
(45) Date of Patent: Apr. 25, 2023

(54) SYSTEM AND METHOD FOR CLINICAL SOIL CONTROL FOR A SKIN GRAFTING SYSTEM

(71) Applicant: Medline Industries, LP, Springfield, IL (US)

(72) Inventors: Kelly Molinaro, Chicago, IL (US); Marvin A. Guiles, Stow, MA (US); Thomas J. Evans, Bedford, MA (US); Aaron McPherson, Boston, MA (US)

(*) Notice: Subject to any disclaimer, the term of this patent is extended or adjusted under 35 U.S.C. 154(b) by 541 days.

(21) Appl. No.: 16/741,535

(22) Filed: Jan. 13, 2020

(65) Prior Publication Data

US 2021/0212711 A1  Jul. 15, 2021

(51) Int. Cl.
*A61B 17/322* (2006.01)
*A61B 17/00* (2006.01)
*A61M 37/00* (2006.01)

(52) U.S. Cl.
CPC ....... *A61B 17/322* (2013.01); *A61M 37/0015* (2013.01); *A61B 2017/00004* (2013.01); *A61B 2017/3225* (2013.01)

(58) Field of Classification Search
CPC ........ A61B 17/322; A61B 2017/00004; A61B 46/10; A61B 2017/3225; A61M 37/0015; A61M 37/0076; A61M 2037/003–0061
See application file for complete search history.

(56) References Cited

U.S. PATENT DOCUMENTS

| | | | |
|---|---|---|---|
| 6,345,553 B1 | 2/2002 | Adler et al. | |
| 6,505,530 B2 | 1/2003 | Adler et al. | |
| 6,997,923 B2 | 2/2006 | Anderson et al. | |
| 9,060,803 B2 | 6/2015 | Anderson et al. | |
| 9,743,949 B2 | 8/2017 | Guiles et al. | |
| 9,827,006 B2 | 11/2017 | Anderson et al. | |
| 9,895,162 B2 | 2/2018 | Anderson et al. | |
| 2005/0137525 A1 | 6/2005 | Wang et al. | |
| 2005/0283141 A1 | 12/2005 | Giovannoli | |
| 2009/0194446 A1* | 8/2009 | Miller ................ | A61B 50/3001 606/86 R |
| 2011/0087177 A2 | 4/2011 | Weston | |
| 2012/0271320 A1 | 10/2012 | Hall et al. | |

(Continued)

FOREIGN PATENT DOCUMENTS

WO   2014028626 A1   2/2014

OTHER PUBLICATIONS

Acelity, Cellutome(TM) Epidermal Harvesting System, https://web.archive.org/web/20210528154715/https://www.acelity.com/healthcare-professionals/global-product-catalog/catalog/cellutome-epidermal-harvesting-system, Copyright 3M 2020, 4 pages.

(Continued)

*Primary Examiner* — Kathleen S Holwerda
*Assistant Examiner* — Serenity A Miller
(74) *Attorney, Agent, or Firm* — Quarles & Brady LLP

(57) ABSTRACT

Systems and methods for controlling clinical soil are provided. A system includes a device cover formed of a flexible polymer sheet defining an interior volume for a skin grafting device, and includes at least a first opening configured to receive a portion of the skin grafting device. The system further includes a cincture having a gasket configured to be affixed to a perimeter of the first opening of the device cover and to secure the device cover about the first opening to the skin grafting device to inhibit fluid ingress into the interior volume of the device cover during a skin grafting process performed using the skin grafting device.

20 Claims, 27 Drawing Sheets

(56) References Cited

U.S. PATENT DOCUMENTS

| | | | |
|---|---|---|---|
| 2015/0201825 A1* | 7/2015 | Na | A61B 1/00133 |
| | | | 600/107 |
| 2015/0216545 A1 | 8/2015 | Anderson et al. | |
| 2015/0335319 A1 | 11/2015 | Chin et al. | |
| 2016/0015416 A1 | 1/2016 | Franco et al. | |
| 2016/0310159 A1* | 10/2016 | Guiles | A61B 17/3205 |
| 2017/0354810 A1* | 12/2017 | O'Brien, III | A61N 1/40 |
| 2018/0000504 A1 | 1/2018 | Knowlton | |
| 2018/0036029 A1 | 2/2018 | Anderson et al. | |
| 2018/0140316 A1 | 5/2018 | Anderson et al. | |
| 2019/0008542 A1 | 1/2019 | Guiles et al. | |
| 2019/0076204 A1* | 3/2019 | Robertson | A61B 17/29 |
| 2019/0090897 A1 | 3/2019 | Ma | |
| 2019/0290378 A1* | 9/2019 | Schwägli | A61B 46/40 |
| 2021/0100572 A1 | 4/2021 | Guiles et al. | |

OTHER PUBLICATIONS

Bellus Medical, SkinPen Microneedling System, Instructions for Use, https://skinpen.com/wp-content/uploads/2018/03/SkinPen-Instructions-For-Use.pdf, Mar. 21, 2018, 16 pages.

Bellus Medical, SkinPen Microneedling, https://web.archive.org/web/20191204092932/https://skinpen.com/, Copyright 2019 Bellus Medical, 4 pages.

KCI Medical, V.A.C. Therapy Advanced Wound Healing by Design, https://web.archive.org/web/20171015053528/http://www.kci-medical.sg/SG-ENG/vactherapy, Oct. 15, 2017, 1 page.

RenovaCare, Inc., SkinGun(TM) and CellMist(TM) Technology Overview, https://web.archive.org/web/20190831012920/https://www.renovacareinc.com/technology/, Copyright 2019 RenovaCare, Inc., 4 pages.

S2medical, Skin Grafting, Instagraft, https://web.archive.org/web/20201130053246/https://www.s2m.se/skin-grafting, Nov. 30, 2020, 2 pages.

Smith + Nephew, Versajet II, Hydrosurgery System, https://www.smith-nephew.com/key-products/advanced-wound-management/versajet/, Sep. 9, 2019, 3 pages.

UltraMIST, UltraMIST for Wound Healing, https://web.archive.org/web/20190630011405/https://www.ultramist.com/, Copyright 2019 Celularity, Inc., 5 pages.

International Searching Authority. International Search Report and Written Opinion, PCT/US2021/012974, dated Apr. 6, 2021, 8 pages.

\* cited by examiner

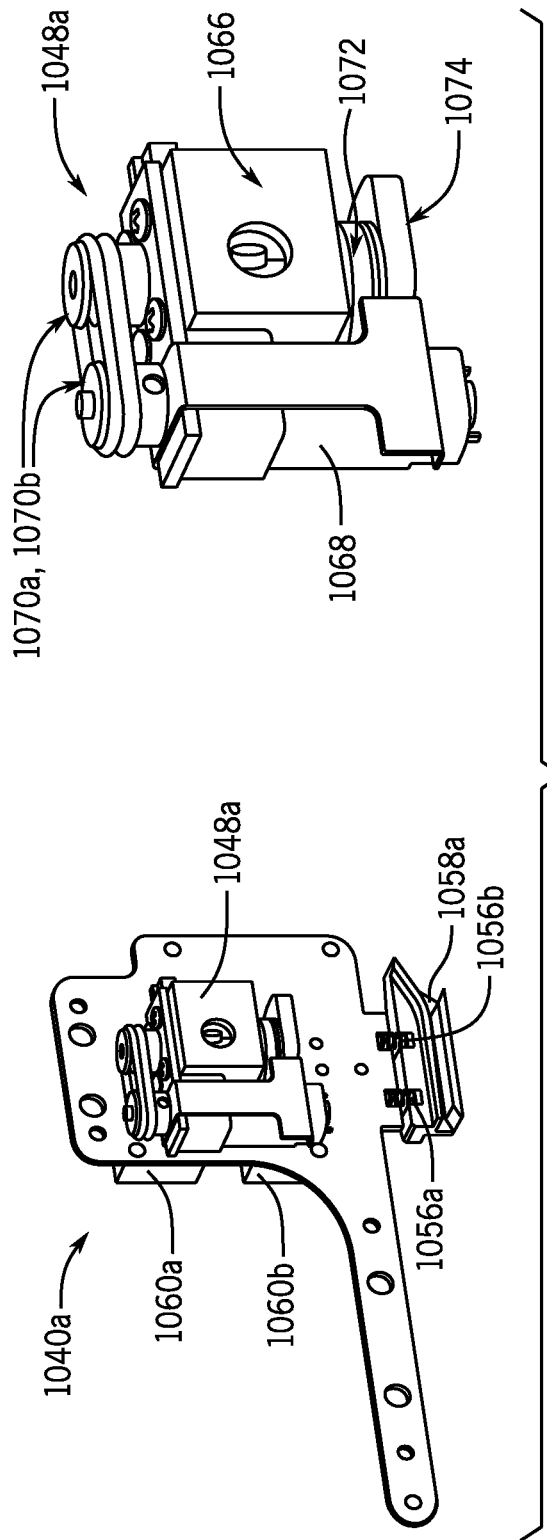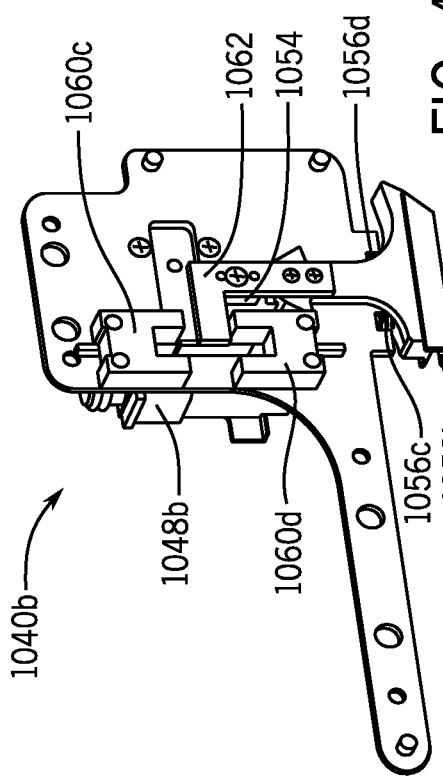
FIG. 4B
FIG. 4C

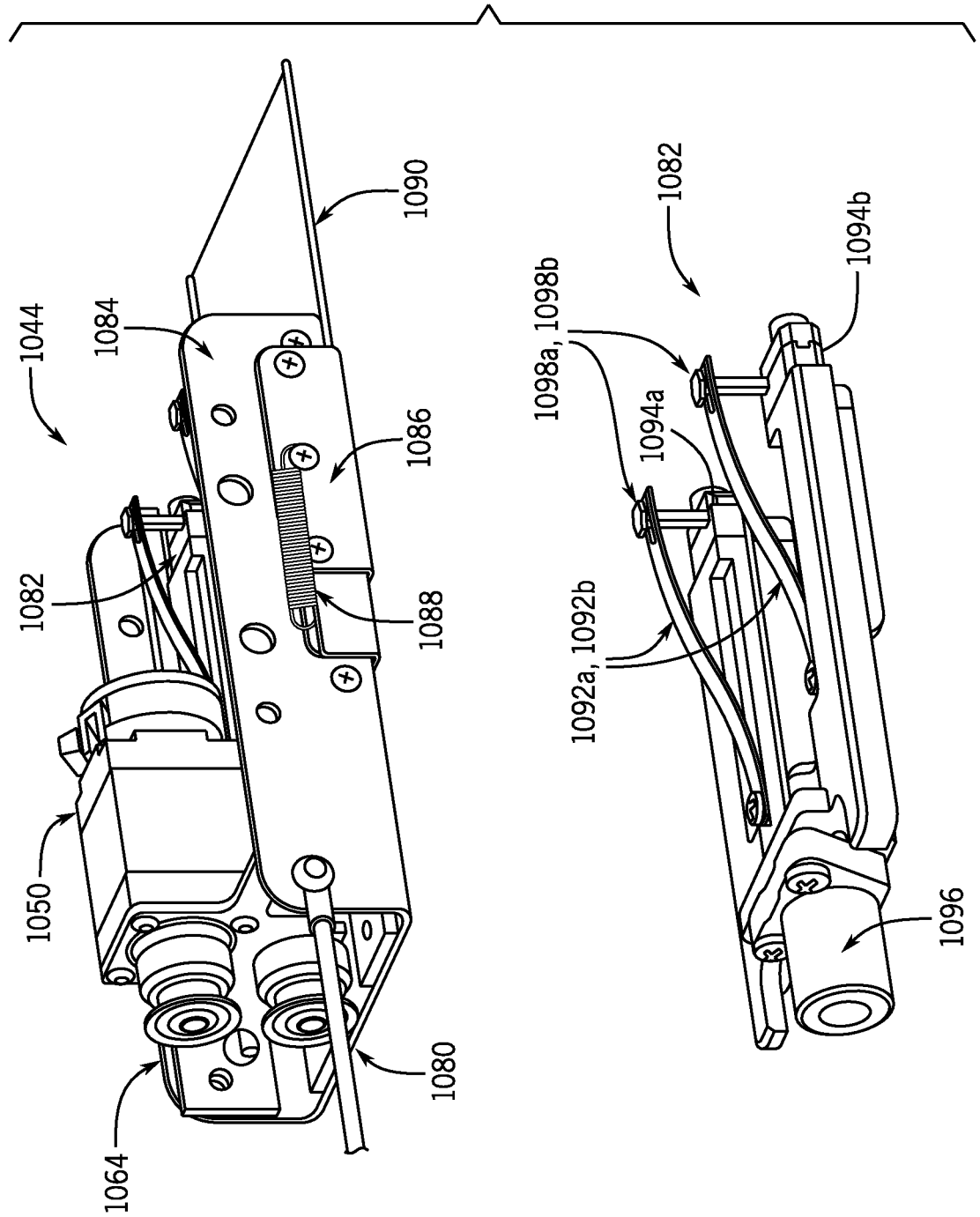

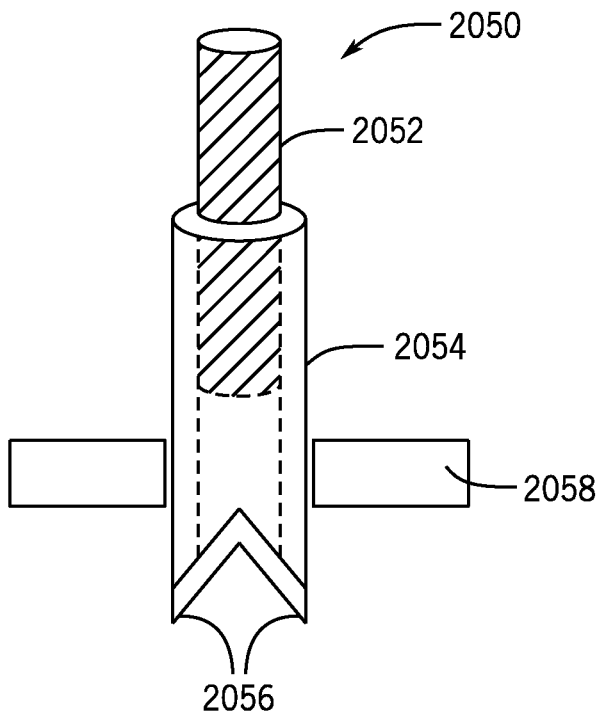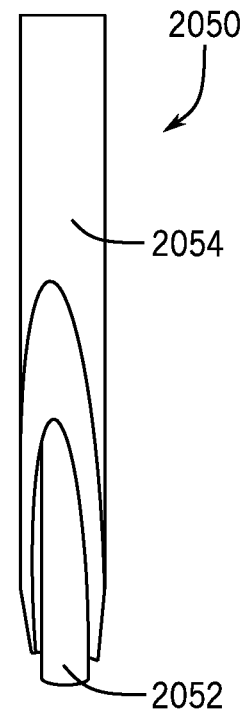
FIG. 6A          FIG. 6B
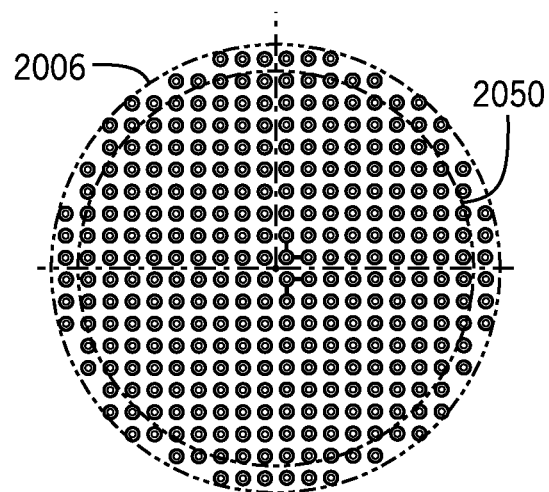
FIG. 6C

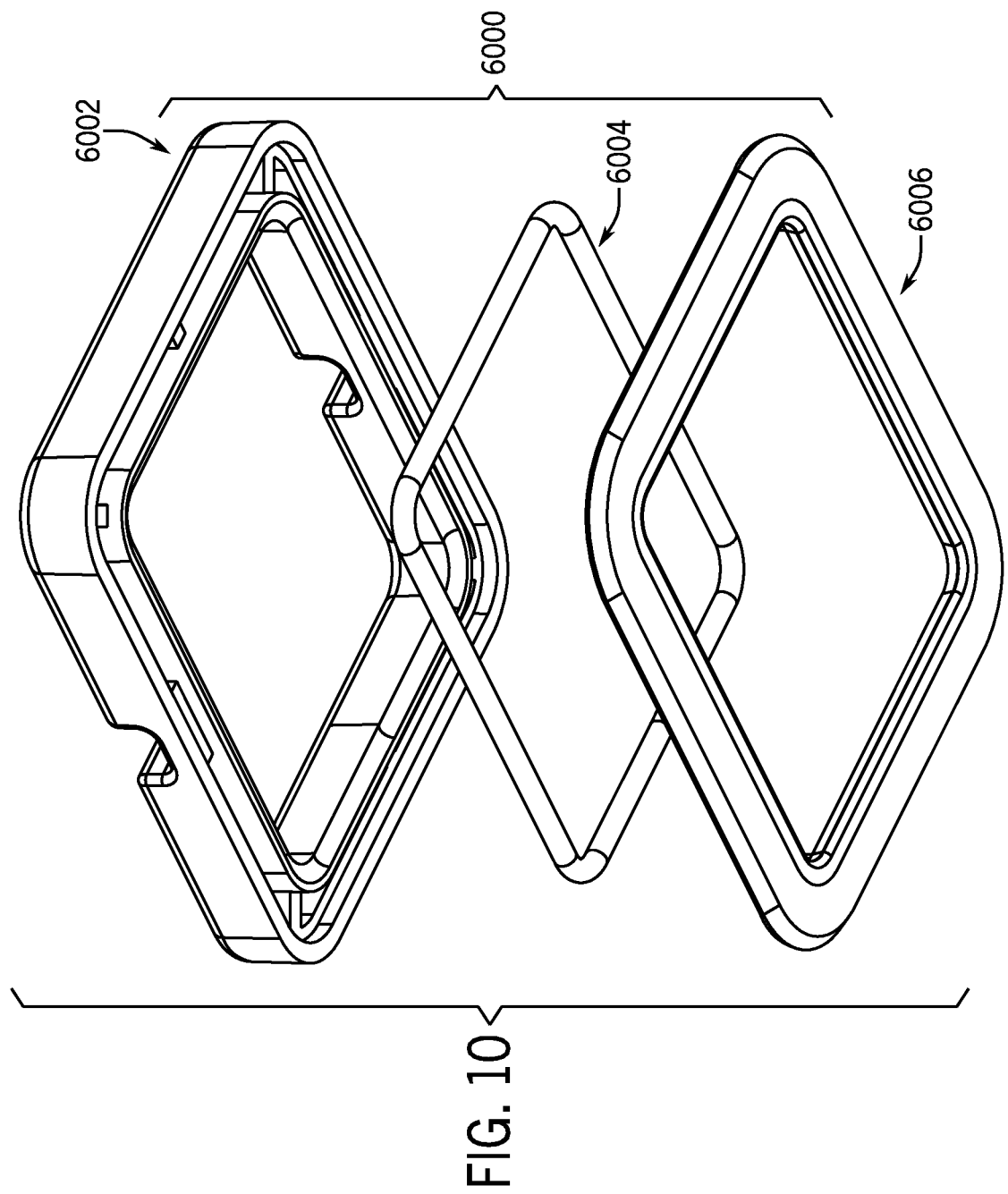

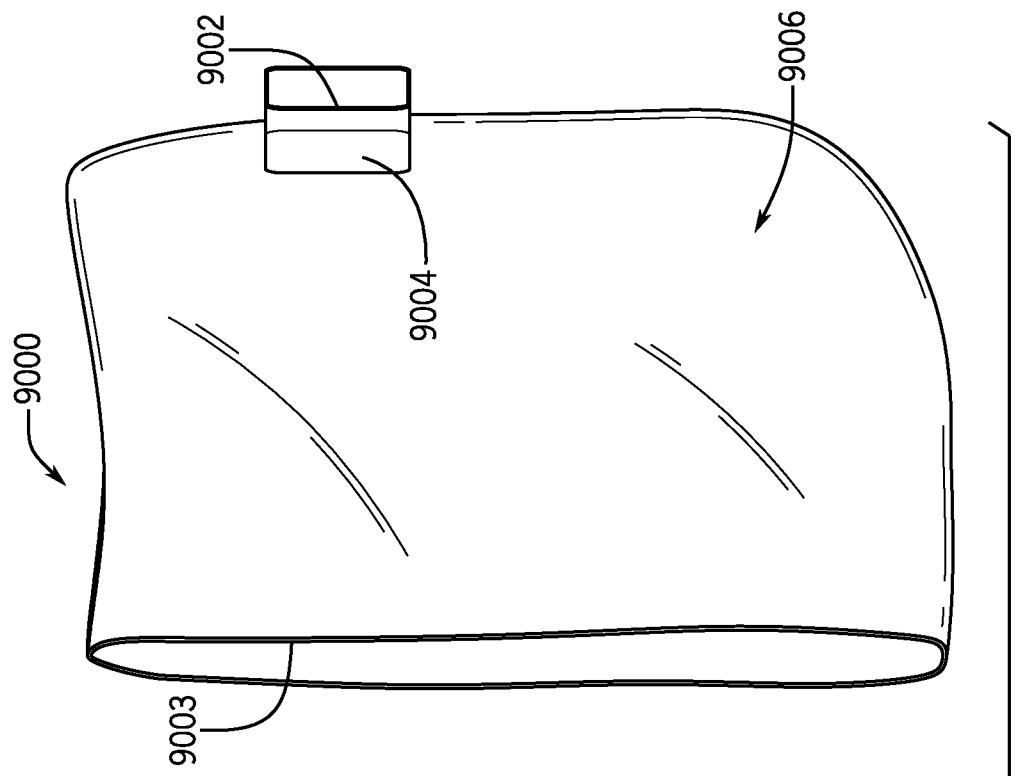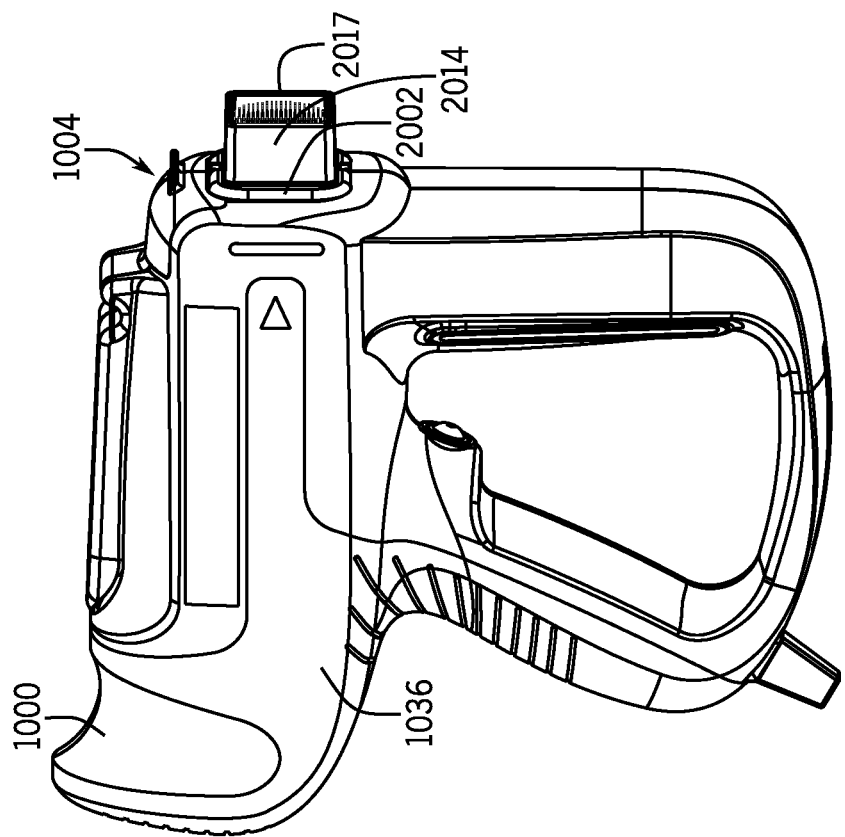
FIG. 16A

SYSTEM AND METHOD FOR CLINICAL SOIL CONTROL FOR A SKIN GRAFTING SYSTEM

BACKGROUND OF THE INVENTION

The subject matter disclosed herein generally relates to a skin grafting system and, more particularly, to a system that may include a device for harvesting and scattering skin microcolumns.

An autograft can refer to tissue transplanted from one part of an individual's body (e.g., a "donor site") to another part (e.g., a "recipient site"). Autografts can be used, for example, to replace missing skin and other tissue and/or to accelerate healing resulting from trauma, wounds, burns, surgery and birth defects. Availability of tissue for autografting can be limited by characteristics of candidate donor sites, including a number and/or total area of tissue grafts, healing behavior of the donor site, similarity of the donor and recipient sites, aesthetic considerations, and the like.

Skin grafting can be performed surgically. For example, a conventional autograft procedure may include excision or surgical removal of burn injured tissue, choosing a donor site, which may be an area from which healthy skin is removed to be used as cover for the cleaned burned area, and harvesting, where the graft may be removed from the donor site (e.g., using an instrument similar to an electric shaver). Such instrument (e.g., a dermatome) can be structured to gently shave a thin piece of tissue (e.g., about $10/1000$ of an inch thick for a split-thickness graft) from the skin at the undamaged donor site to use as a skin graft. The skin graft can then be placed over the cleaned wound to heal. Donor skin tissue can be removed to such a depth that the donor site can heal on its own, in a process similar to that of healing of a second degree burn.

Traditionally, sheet grafts and meshed grafts are the two types of autografts often used for a permanent wound coverage. A sheet graft can refer to a piece of skin tissue removed from an undamaged donor site of the body, in a process that may be referred to as harvesting. The size of the donor skin piece that is used may be about the same size as the damaged area. The sheet graft can be applied over the excised wound, and stapled or otherwise fastened in place. The donor skin tissue used in sheet grafts may not stretch significantly, and a sheet graft can be obtained that is slightly larger than the damaged area to be covered because there may often be a slight shrinkage of the graft tissue after harvesting.

Sheet grafts can provide an improved appearance of the repaired tissue site. For example, sheet grafts may be used on large areas of the face, neck and hands if they are damaged, so that these more visible parts of the body can appear less scarred after healing. A sheet graft may be used to cover an entire burned or damaged region of skin. Small areas of a sheet graft can be lost after placement because a buildup of fluid (e.g., a hematoma) can occur under the sheet graft following placement of the sheet graft.

A meshed skin graft can be used to cover larger areas of open wounds that may be difficult to cover using sheet grafts. Meshing of a skin graft can facilitate skin tissue from a donor site to be expanded to cover a larger area. It also can facilitate draining of blood and body fluids from under the skin grafts when they are placed on a wound, which may help prevent graft loss. The expansion ratio (e.g., a ratio of the unstretched graft area to the stretched graft area) of a meshed graft may typically be between about 1:1 to 1:4. For example, donor skin can be meshed at a ratio of about 1:1 or 1:2 ratio, whereas larger expansion ratios may lead to a more fragile graft, scarring of the meshed graft as it heals, and/or extended healing times.

A conventional graft meshing procedure can include running the donor skin tissue through a machine that cuts slits through the tissue, which can facilitate the expansion in a pattern similar to that of fish netting or a chain-link fence. Healing can occur as the spaces between the mesh of the stretched graft, which may be referred to as gaps or interstices, fill in with new epithelial skin growth. However, meshed grafts may be less durable graft than sheet grafts, and a large mesh can lead to permanent scarring after the graft heals.

As an alternative to autografting, skin tissue obtained from recently-deceased people (which may be referred to, e.g. as a homograft, an allograft, or cadaver skin) can be used as a temporary cover for a wound area that has been cleaned. Unmeshed cadaver skin can be put over the excised wound and stapled in place. Post-operatively, the cadaver skin may be covered with a dressing. Wound coverage using cadaveric allograft can then be removed prior to permanent autografting.

A xenograft or heterograft can refer to skin taken from one of a variety of animals, for example, a pig. Heterograft skin tissue can also be used for temporary coverage of an excised wound prior to placement of a more permanent autograft, and may be used because of a limited availability and/or high expense of human skin tissue. In some cases religious, financial, or cultural objections to the use of human cadaver skin may also be factors leading to use of a heterograft. Wound coverage using a xenograft or an allograft is generally a temporary procedure which may be used until harvesting and placement of an autograft is feasible.

Harvesting of the graft tissue from the donor site can generally generate undesirable large-scale tissue damage to the donor site. On the other hand, small areas of skin wounding adjacent to healthy tissue can be well-tolerated, and may heal quickly. Such healing of small wounds can occur in techniques such as "fractional photothermolysis" or "fractional resurfacing," in which patterns of damage having a small dimension can be created in skin tissue. These exemplary techniques are described, for example, in U.S. Pat. No. 6,997,923. Small-scale damage patterns can heal quickly by regrowth of healthy tissue, and can further provide desirable effects such as skin tightening without visible scarring.

The mechanism of tissue grafting presents the opportunity for grafting tools to be exposed to clinical "soil" (e.g., blood, tissue, hair, etc.) from the patient. In split-thickness and full-thickness skin grafting (both of which harvest tissue that extends below the epidermis), localized damage to capillaries and/or blood vessels often leads to bleeding. The degree of bleeding can be influenced by patient factors, such as, for example, anticoagulant medications.

Therefore, it would be advantageous to have further systems and methods to protect reusable clinical tools from clinical soil, without sacrificing functionality of the skin harvesting process.

BRIEF DESCRIPTION OF THE DISCLOSURE

In accordance with some implementations of the present disclosure, a skin grafting system is provided. The skin grafting system includes a handheld device including a device housing forming an interior that secures a drive system. The skin grafting system further includes a cartridge having a plurality of hollow microneedles surrounded by a peripheral housing and configured to be operated by the handheld device to extend and retract during a skin grafting process. Additionally, the skin grafting system includes an absorptive material disposed within the peripheral housing and surrounding the plurality of hollow microneedles, and a device cover formed of a flexible polymer sheet defining an interior volume for the handheld device. The device cover includes at least a first opening configured to receive the cartridge. The skin grafting system further includes a cincture. The cincture includes a gasket configured to be affixed to a perimeter of the first opening of the device cover and to secure the device cover about the first opening to at least one of the handheld device or the cartridge to inhibit fluid ingress into the interior volume of the device cover. Additionally, the absorptive material is configured to inhibit fluid ingress into the interior of the handheld device via the cartridge.

In accordance with some implementations of the present disclosure, a skin grafting system is provided. The system includes a handheld device having a device housing forming an interior that secures a drive system. The system further includes a cartridge having a plurality of hollow microneedles surrounded by a peripheral housing and configured to be operated by the drive system to extend and retract during a skin grafting process. Additionally, the system includes a device cover formed of a flexible polymer sheet defining an interior volume for the handheld device, and including at least a first opening configured to receive the cartridge. The system further includes a cincture including a gasket configured to be affixed to a perimeter of the first opening of the device cover and to secure the device cover about the first opening to at least one of the handheld device or the cartridge to inhibit fluid ingress into the interior volume of the device cover.

In accordance with some implementations of the present disclosure, a system for controlling clinical soil is provided. The system includes a device cover formed of a flexible polymer sheet defining an interior volume for a skin grafting device, and includes at least a first opening configured to receive a portion of the skin grafting device. The system further includes a cincture having a gasket configured to be affixed to a perimeter of the first opening of the device cover and to secure the device cover about the first opening to the skin grafting device to inhibit fluid ingress into the interior volume of the device cover during a skin grafting process performed using the skin grafting device.

The following description and the accompanying drawings set forth in detail certain illustrative embodiments of the present disclosure. However, these embodiments are indicative of but a few of the various ways in which the principles of the disclosure can be employed. Other embodiments and features will become apparent from the following detailed description of the present disclosure when considered in conjunction with the drawings.

BRIEF DESCRIPTION OF THE DRAWINGS

The descriptions hereafter are provided with reference to the accompanying drawings, wherein like reference numerals denote like elements.

FIG. 4B is a right perspective view of a left frame assembly corresponding to the internal assembly of FIG. 4A, in accordance with some implementations of the present disclosure.

FIG. 4C is a right perspective view of a right frame assembly corresponding to the internal assembly of FIG. 4A, in accordance with some implementations of the present disclosure.

FIG. 4D is a rear perspective view of a horizontal component assembly corresponding to the internal assembly of FIG. 4A, in accordance with some implementations of the present disclosure.

FIG. 6A is an example of a microneedle and pin assembly that can harvest tissue, in accordance with some implementations of the present disclosure.

FIG. 6B is a perspective view of a microneedle and pin assembly that can harvest tissue, in accordance with some implementations of the present disclosure.

FIG. 6C is a plan view of a microneedle array, in accordance with some implementations of the present disclosure.

FIG. 10 is an exploded view of a gasket assembly corresponding to a clinical soil control system, in accordance with some implementations of the present disclosure.

FIG. 16A is a side view of a clinical soil control system, in accordance with some implementations of the present disclosure.

DETAILED DESCRIPTION OF THE DISCLOSURE

Figure 1:
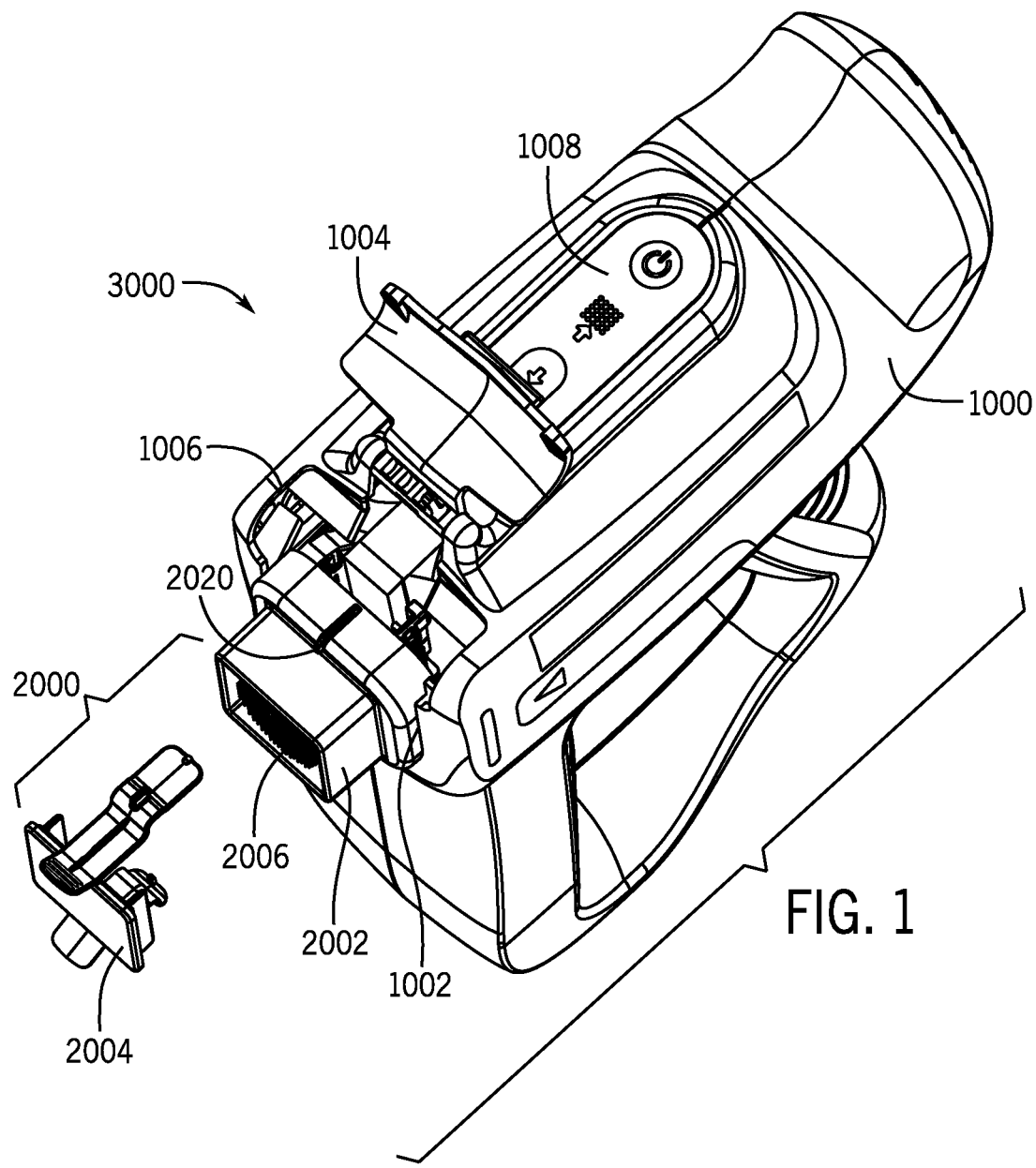
FIG. 1 is a top perspective view of a skin grafting system, including a cartridge, in accordance with some implementations of the present disclosure.

The following discussion is presented to enable a person skilled in the art to make and use the systems and methods of the present disclosure. Various modifications to the illustrated embodiments will be readily apparent to those skilled in the art, and the high-level principles herein can be applied to other embodiments and applications without departing from embodiments of the present disclosure. Thus, embodiments of the present disclosure are not intended to be limited to embodiments shown, but are to be accorded the widest scope consistent with the principles and features disclosed herein.

The detailed description is to be read with reference to the figures. The figures depict selected embodiments and are not intended to limit the scope of embodiments of the present disclosure. Skilled artisans will recognize the examples provided herein have many useful alternatives and fall within the scope of embodiments of the present disclosure. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. As used herein, unless expressly stated otherwise, "connected" means that one element/feature is directly or indirectly connected to another element/feature, and not necessarily electrically or mechanically. Likewise, unless expressly stated otherwise, "coupled" means that one element/feature is directly or indirectly coupled to another element/feature, and not necessarily electrically or mechanically.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., digital signal processing elements, logic elements, diodes, etc., which may carry out a variety of functions under the control of one or more processors or other control devices. Other embodiments may employ program code, or code in combination with other circuit components.

As described above, the present disclosure generally relates to a skin grafting system and, more particularly, to a system that may include a device for harvesting and scattering skin microcolumns. In some situations, the process of harvesting the skin microcolumns can include penetrating donor site tissue. Although generally minimal, harvesting the microcolumns often causes localized bleeding. Blood quantity from the donor site can depend on a variety of factors, such as, for example, number of tissue punctures/penetrations, number of harvesting processes conducted on a single tissue area, number of harvesting processes conducted with a single cartridge (as described below), patient blood pressure, platelet count, medication, donor site treatments, and/or comorbidities. In some situations, it may be advantageous to prevent blood contact and/or ingress into portions of the skin grafting system. In particular, it may be advantageous to prevent blood ingress to reusable elements of the skin grafting system.

As an example, healthcare facilities often have standard cleaning, disinfecting, and/or sterilization procedures that must be performed when an instrument is reusable between patients. Specifically, to minimize the risk of spread of infection, all blood and body substances should be treated as potentially infectious. With complex instruments, blood ingress into an instrument housing can result in procedure delays, lengthy sterilization processes, and/or instrument replacement (and associated cost), among other things. Accordingly, the present disclosure includes systems for preventing blood ingress into a handheld device (e.g., a reusable handheld device) corresponding to a skin grafting system. Systems for preventing blood/fluid ingress into a skin grafting system are further described in U.S. patent application Ser. No. 16/592,312, filed on Oct. 3, 2019, and entitled "System and Method for Fluid Ingress Control for a Skin Grafting System," the entire disclosure of which is incorporated herein by reference.

In some implementations, systems for preventing blood or fluid ingress into a skin grafting system can include a cincture. As used herein, the term cincture is defined as an element which partially or entirely encircles or encloses (e.g., forming a seal, attaching otherwise disjoint components). Additionally, as used herein, the term seal is defined as a contact point between elements, the contact point creating a barrier to help prevent fluid ingress.

Referring now to FIG. 1, a skin grafting system 3000 is shown, in accordance with some implementations of the present disclosure. In some configurations, the skin grafting system 3000 can be configured to harvest and scatter donor tissue. As shown, the skin grafting system 3000 can include a handheld device 1000 (which can be reusable) and a cartridge assembly 2000. As will be described in greater detail below, the cartridge assembly 2000 can include a cartridge 2002 and a cartridge cover 2004. The cartridge 2002 can include a microneedle and pin array 2006, according to some configurations. Notably, the cartridge 2002 can include a simplified microneedle array 2006 (i.e., without pins).

Figure 2B:
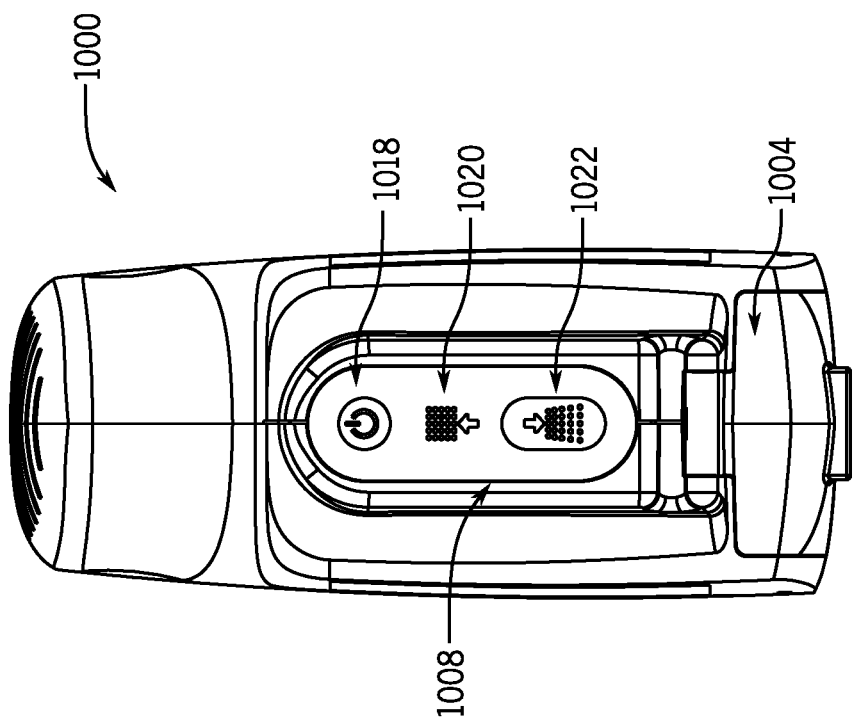
FIG. 2B is a top view of a user interface that may be included in the system of FIG. 2A, in accordance with some implementations of the present disclosure.
Figure 2A:
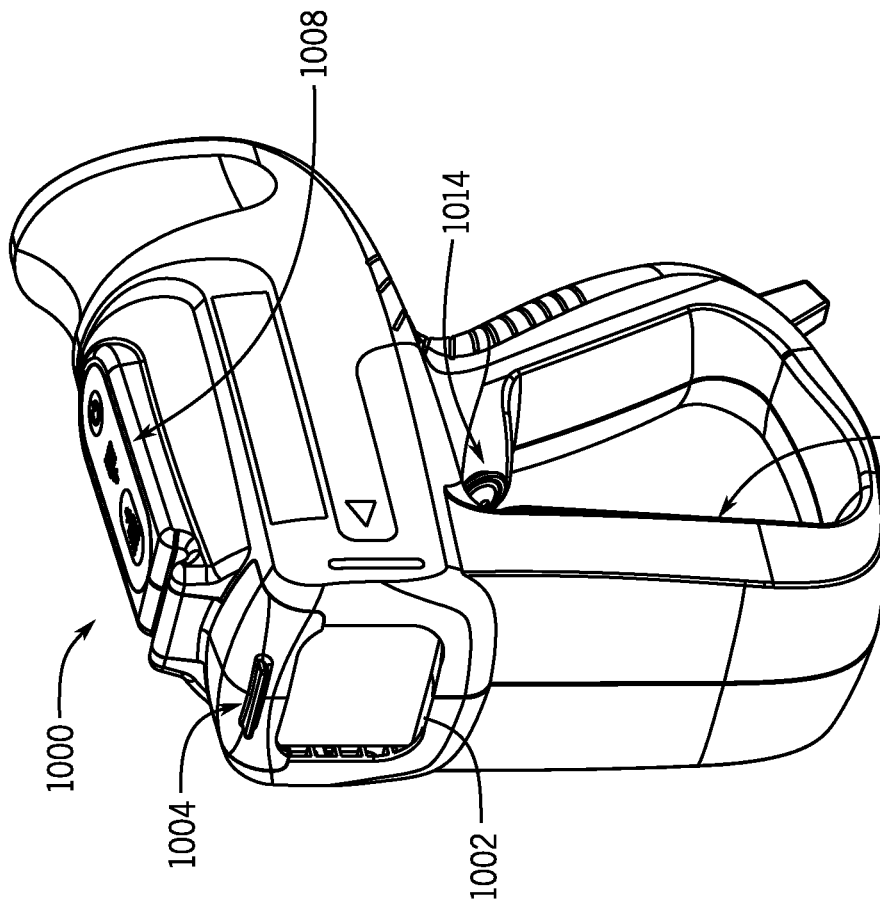
FIG. 2A is a front perspective view of the system of FIG. 1.

As shown by FIGS. 1-2B, the handheld device 1000 can include an engagement slot 1002 configured to receive the cartridge assembly 2000. A loading door 1004 can move between an "open" position (see, e.g., FIG. 1) and a "closed" position (see, e.g., FIGS. 2A-2B). In some configurations, the loading door 1004 can be hinged and further configured to open and close over a loading aperture 1006. The handheld device 1000 can include a door sensor, which can determine the position of the loading door 1004. The loading aperture 1006 can be sized such that the cartridge assembly 2000 can slide in and out of the engagement slot 1002, as desired by the user. Advantageously, the cartridge assembly 2000 can be single-use and/or disposable (including, for example, multiple uses for a single patient), while the handheld device 1000 can be designed to be multi-use. As shown by FIG. 2A, the handheld device 1000 can further include a trigger 1014. The trigger 1014 can be configured to activate a harvesting process and/or a scattering process in response to selection via a user interface 1008 and/or trigger inputs by a user. In some configurations, the handheld device 1000 can include an indicator light 1016. The indicator light 1016 can be positioned such that a user can readily view the indicator light 1016 during harvesting and/or scattering.

In some configurations, the handheld device 1000 can include a user interface 1008. As shown, the user interface 1008 can include a stand-by input 1018, an indicator light 1020, and/or a scatter input 1022. In some configurations, the indicator light 1020 can operate the same as, or similar to, the indicator light 1016 (as described above). The stand-by input 1018, the indicator lights 1016, 1020, and the scatter input 1022 can provide visual feedback to a user that correspond to current operation of the skin grafting system 3000 as the skin grafting system 3000 is utilized according to a skin grafting process, such as will be described.

Figure 3A:
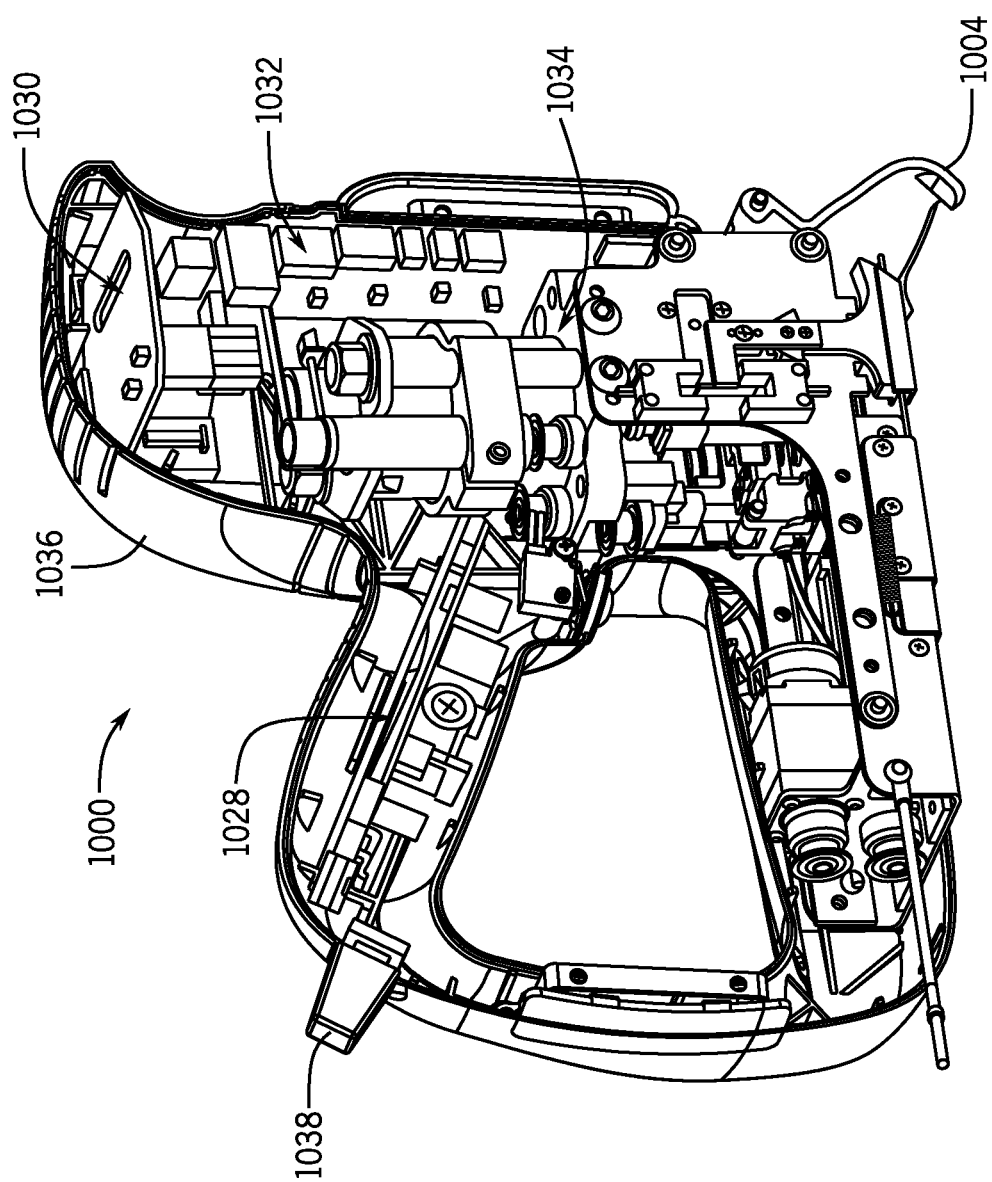
FIG. 3A is a cutaway view of the handheld device of FIG. 2A, in accordance with some implementations of the present disclosure.
Figure 3B:
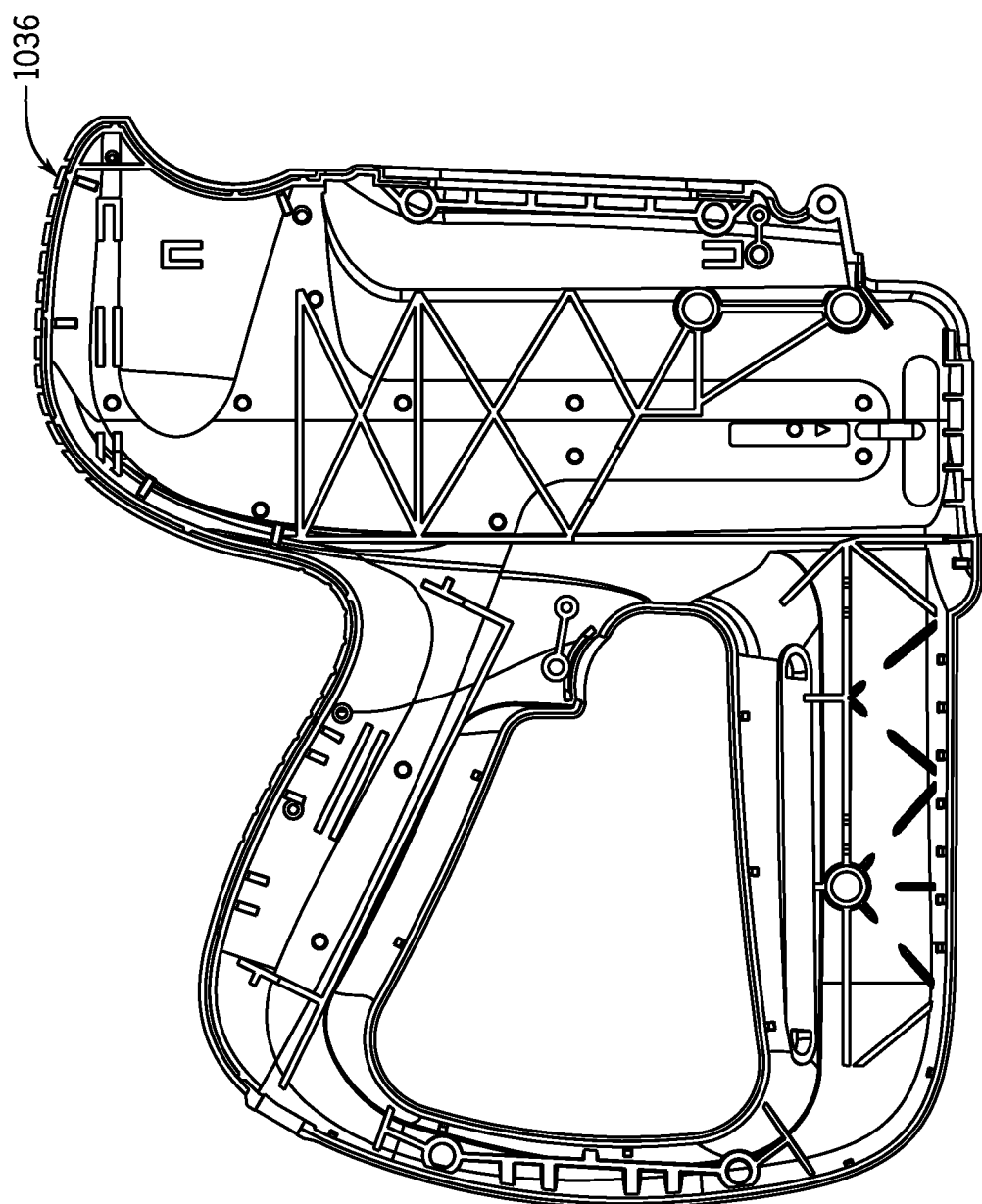
FIG. 3B is a cutaway view of a housing corresponding to the handheld device of FIG. 2A, in accordance with some implementations of the present disclosure.

Referring now to FIGS. 3A-3B, cutaway views of the handheld device 1000 are shown, according to configurations of the present disclosure. The handheld device 1000 is shown to include various internal controllers. In some configurations, the handheld device 1000 can include a power module 1028, a solenoid controller 1030, and/or a main controller 1032. The power module 1028 can be in electrical communication with a power input 1038. In some configurations, a drive system 1034 can include a solenoid in communication with the solenoid controller 1030.

Still referring to FIGS. 3A-3B, in some configurations, the handheld device 1000 can include a housing 1036. The housing 1036 can include a left enclosure half and a right enclosure half. In some configurations, each of the left enclosure half, the right enclosure half, the loading door 1004 and the enclosure mount cover can be individually injection molded. The left and right enclosure halves can be made up of a hard plastic substrate, and in some configurations, a softer elastomeric over-molded section. Similarly, the loading door 1004 and the enclosure mount cover can be made up of hard plastic substrate. In some configurations, the interior of the housing 1036 can interface with internal subassemblies. As an example, ribs can be affixed to the interior of the housing 1036, and can be configured to support various printed circuit boards (PCBs). The ribs can separate the PCBs (e.g., power module 1028, solenoid controller 1030, and main controller 1032) from internal moving components. Additionally, in some configurations, the housing 1036 can support the internal subassembly 1034 via pins and vibration damping boots. This can dampen the operational impacts of the internal subassembly 1034 (e.g., from a user, from internal moving components), as well as protect the internal subassembly 1034 from damage due to external impacts (e.g., from dropping the handheld device 1000.

Figure 4A:
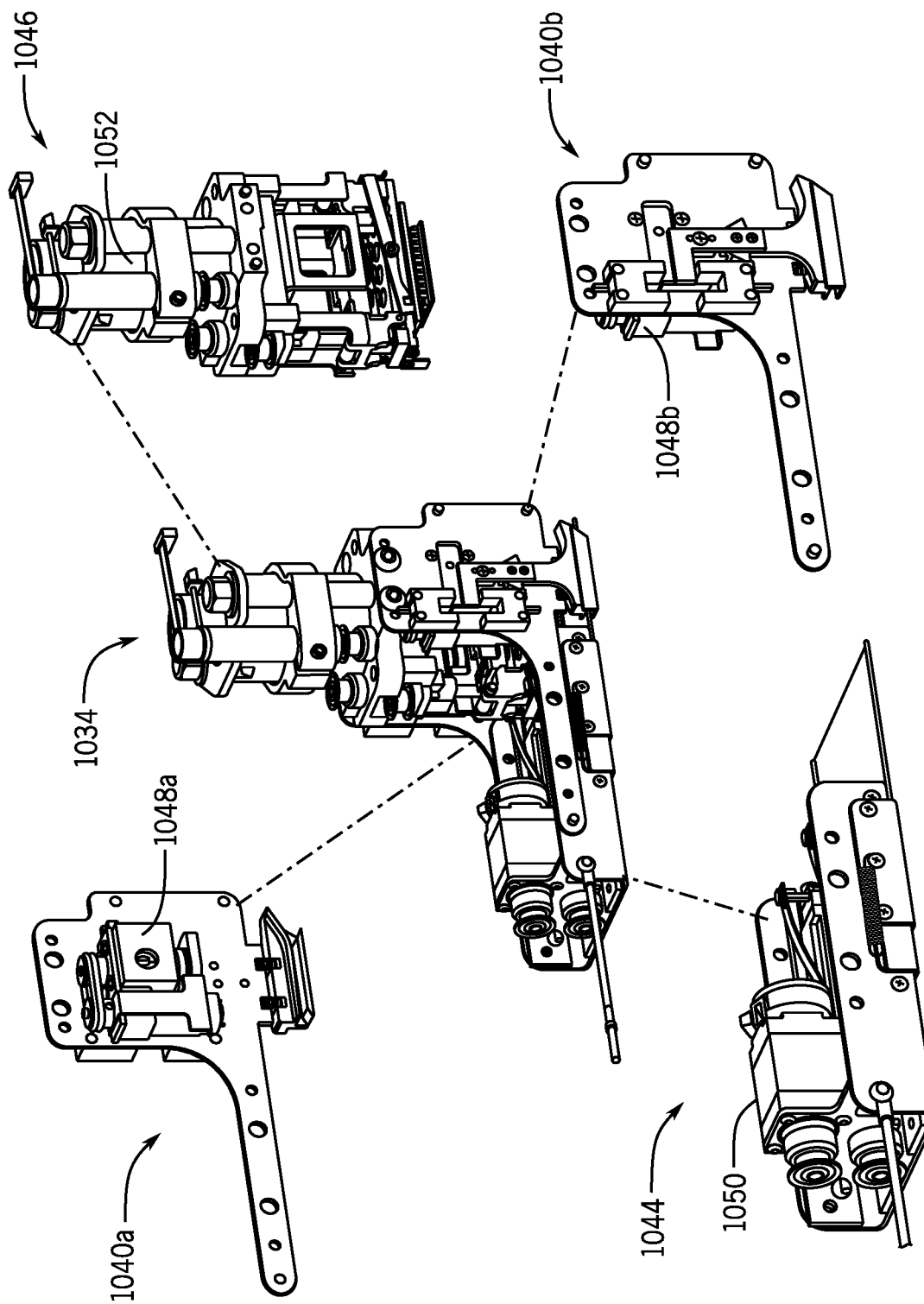
FIG. 4A is a rear perspective view of an internal drive assembly and related elements corresponding to the handheld device of FIG. 2A, in accordance with some implementations of the present disclosure.

Referring now to FIGS. 4A-4E, various internal assemblies corresponding to handheld device 1000 are shown, according to some configurations. FIG. 4A shows the internal subassembly 1034 that can include a left frame assembly 1040a, a right frame assembly 1040b, a horizontal component assembly 1044, and/or a vertical component assembly 1046. Each of the left and right frame assemblies 1040a, 1040b can include a corresponding flipper assembly (e.g., left flipper assembly 1048a, right flipper assembly 1048b). In some configurations, the horizontal component assembly 1044 can include a horizontal motor 1050. Further, the vertical component assembly 1046 can include a solenoid 1052.

Still referring to FIGS. 4A-4E, and in particular FIGS. 4B-4C, further exemplary details of the left and right frame assemblies 1040a, 1040b are shown, according to some configurations. In some configurations, the left frame assembly 1040a and the right frame assembly 1040b can be the same or substantially similar (e.g., symmetrical). As shown, the left frame assembly 1040a can include a left flipper assembly 1048a affixed to a first side of a left frame. Additionally, the left frame assembly 1040a can include flag sensors 1060a, 1060b, affixed to a second side of the left frame. The flag sensors 1060a, 1060b can communicate with a position sensing linear slide 1054, and a position sensing flag 1062. In some configurations, the left frame assembly 1040a can include position sensing springs 1056a, 1056b, which can contact a tissue interface 1058a. The tissue interface 1058a can be positioned on a third side of the left frame. In some configurations, the left frame assembly 1040a can attach to a portion of the vertical component assembly 1046 via screws and alignment pins, or other attachment systems.

In some configurations, the right frame assembly 1040b can include flag sensors 1060c, 1060d, affixed to a first side of a right frame. The flag sensors 1060c, 1060d can communicate with a position sensing linear slide 1054, and a position sensing flag 1062. Additionally, as shown, the right frame assembly 1040b can include a right flipper assembly 1048b affixed to a second side of the right frame. In some configurations, the right frame assembly 1040b can include position sensing springs 1056c, 1056d, which can contact a tissue interface 1058b. The tissue interface 1058b can be positioned on a third side of the right frame. In some configurations, the right frame assembly 1040b can attach to a portion of the vertical component assembly 1046 via screws and alignment pins.

The flipper assemblies 1048a, 1048b can include a flipper mounting block 1066, and a flipper motor 1068. In some configurations, the flipper mounting block 1066 can be constructed from a dielectric material. The flipper motor 1068 can be connected to (and control) flipper driver pulleys 1070a, 1070b. A bearing (e.g., a thrust bearing) 1072 can support an axial load exerted by the needle top plate (e.g., needle top plate 1112 as described below) on a flipper 1074. The flipper 1074 can rotate in accordance with motor actuation, and the flipper driver pulleys 1070a, 1070b can prevent any downward movement of the flipper 1074 during operation of the handheld device 1000. In some configurations, the flipper 1074 can include two connected components, such as two brass components that are brazed together. The primary function of the flipper 1074 can be to hold a needle top plate 1112 of FIG. 4E in place when loading needle retract springs. The flipper 1074 can then move out of the way of the needle top plate 1112 during the remainder of normal operation. In some configurations, the flipper mounting block 1066 can act as a guide for solenoid plunger bar 1106 of FIG. 4E (e.g., to keep proper alignment).

Still referring to FIGS. 4A-4E, and in particular FIG. 4D, further exemplary details of the horizontal component assembly 1044 are shown, according to some configurations. The horizontal component assembly can include sensors, actuators, and/or guides for positioning a horizontal carriage assembly 1082 and, thereby, the hammers 1098a, 1098b used to drive microneedles into the tissue (as will be described below). In some configurations, a horizontal flag sensor 1064 can be used to position the horizontal component assembly 1082. As shown, the horizontal component assembly 1044 can include the horizontal carriage assembly 1082 that can be configured to mount the horizontal motor 1050. In some configurations, a horizontal chassis 1084 can support the horizontal carriage assembly 1082. Additionally, the right frame assembly 1040b and the left frame assembly 1040a can be affixed to opposing sides of the horizontal chassis 1084, for example, using rivets. An earth-ground connection 1080 can be attached to the horizontal chassis 1084, according to some configurations.

In some configurations, the horizontal component assembly 1044 can further include a retractable slide door 1090. The slide door 1090 can extend across the loading aperture 1006 when the cartridge 2002 has not been inserted into the engagement slot 1002. Accordingly, a user can be prevented from placing anything into the handheld device 1000 during the absence of the cartridge 2002. The sliding door 1090 can be secured to a sliding door mount 1086, which can be affixed to the horizontal chassis 1084. Additionally, a sliding door spring 1088 can be secured to the sliding door mount 1086, and biased such that the slide door 1090 remains in a "closed" position (i.e., extended across the loading aperture 1006) when a cartridge is not loaded.

As shown, the horizontal carriage assembly 1082 can include hammers 1098a, 1098b, corresponding hammer return springs 1092a, 1092b, and corresponding hammer guides 1094a, 1094b, according to some configurations. Generally, the horizontal carriage assembly 1082 can be configured to position and guide the hammers 1098a, 1098b to drive the microneedles into the tissue. In some configurations, the hammer guides 1094a, 1094b can be made of bronze, which can help to maintain bearing surfaces throughout many harvesting and scattering cycles. Additionally, in some configurations, the hammers 1098a, 1098b can be hardened 17-4 stainless steel, which can provide superior wear characteristics while maintaining anti-corrosion properties. Alternatively, the hammers 1098a, 1098b can be a different bearing material. The horizontal carriage assembly 1082 can further include a horizontal leadscrew drive nut 1096. Additionally, the horizontal leadscrew assembly 1096 can be a Teflon-coated lead screw, and an Acetal drive nut designed to reduce friction. Alternatively, the horizontal leadscrew assembly 1096 can include other material types. The horizontal leadscrew assembly 1096 can provide a pitch adequate for positional resolution and linear force. The horizontal carriage assembly 1082 can additionally use motor stalling to sense whether or not a cartridge is loaded, or if there is a device jam.

Figure 4E:
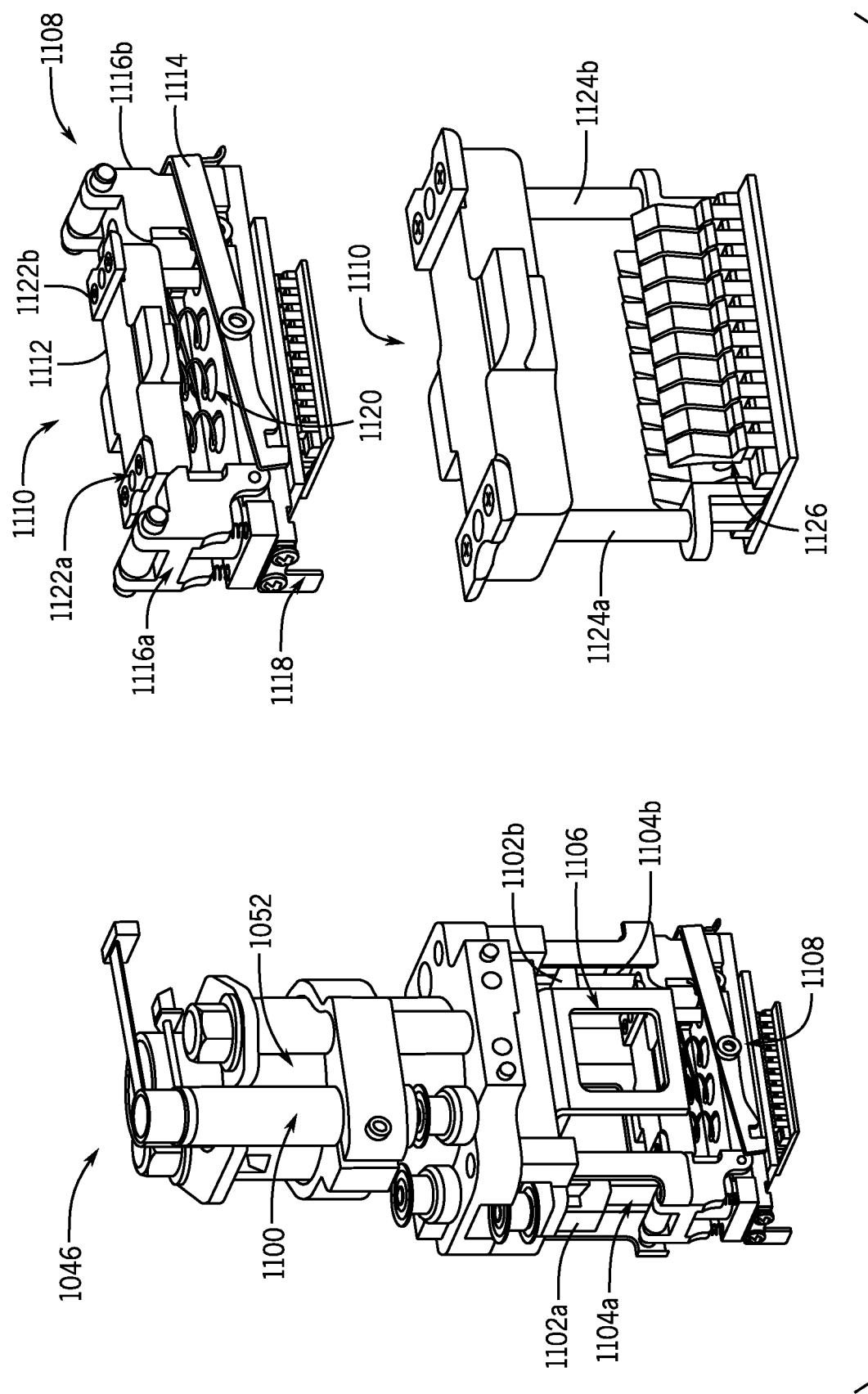
FIG. 4E is a rear perspective view of a vertical component assembly corresponding to the internal assembly of FIG. 4A, in accordance with some implementations of the present disclosure.

Still referring to FIGS. 4A-4E, and in particular FIG. 4E, further exemplary details of the vertical component assembly 1046 are shown, according to some configurations. As shown, the vertical component assembly 1046 can include the solenoid 1052 and corresponding solenoid plunger bar 1106. Additionally, the vertical component assembly 1046 can include a vertical motor 1100, and associated unlock cams 1102a, 1102b and vertical leadscrews 1104a, 1104b. In some configurations, the vertical position of the vertical carriage subassembly 1108 can be controlled by traveling up and down on the vertical leadscrews 1104a, 1104b (e.g., using the vertical motor 1100). As will be described, vertical positioning can move each of the microneedles corresponding to the cartridge 2002. In general, the vertical component assembly 1046 can be configured to interface with and manipulate the cartridge 2002 and its associated components during harvesting and/or scattering of tissue. In some configurations, the vertical motor 1100 can be sized to fit within the vertical component assembly 1046 while still providing the torque and speeds necessary for manipulating the microneedle positions.

In some configurations, the solenoid 1052 can deliver an operating force to the hammers 1098a, 1098b during harvesting. The solenoid 1052 can be activated by a half wave of AC current, as one non-limiting example. The force delivered by the solenoid 1052 can increase sharply, towards the end of its stroke. In some configurations, the mass of the solenoid plunger bar 1106 and the solenoid plunger can be selected based on the energy needed to drive the microneedles into the tissue. In some configurations, a stop (e.g., a brass stop) can be integrated into the solenoid 1052, which can enable extension control of the solenoid plunger bar 1106 and absorption of remaining kinetic energy at the end of the stroke.

In some configurations, the vertical component assembly 1046 can include a vertical carriage assembly 1108. As shown, the vertical carriage assembly 1108 can include a needle retract slide 1110 with a top plate 1112. In some configurations, opposite ends of the vertical carriage assembly 1108 can include needle retract slide-latches 1116a, 1116b with corresponding latch plates 1122a, 1122b. The latch plates 1122a, 1122b can define a maximum position of the needle retract slide 1110. Additionally, needle retract springs 1120 can be integrated into the vertical carriage assembly 1108, such that efficient retraction of the microneedles can be achieved over the pins. The needle retract slide-latches 1116a, 1116b can be used to lock down the needle retract slide 1110 in preparation for harvesting. The vertical carriage assembly 1108 can also move both the needles and pins (e.g., pins within the microneedles) at the same time.

In some configurations, the vertical carriage assembly 1108 can include a cartridge latch 1114, which can be configured to secure the cartridge 2002 upon insertion into the loading aperture 1006. Additionally, a vertical flag 1118 can be affixed to the exterior of the vertical carriage assembly 1108, according to some configurations. As shown, the needle retract slide 1110 can further include guideposts 1124a, 1124b, which can be configured to guide the needle retract slide 1110 during vertical movement. In some configurations, the needle retract slide 1110 can include lockdown latches 1126, which can be in contact with the guideposts 1124a, 1124b, and configured to engage and disengage the microneedles during operating of the handheld device 1000. The needle retract slide 1110 can be a spring loaded subassembly that serves at least two purposes. First, the slide 1110 can lock needle modules down (after being driven into the tissue). Second, the slide 1110 can retract the needles. In some configurations, the needle retract slide 1110 is only capable of retracting the needles, and cannot move the needles forward. Additionally, in some configurations, the lockdown latches 1126 may be only functional after the skin grafting system 3000 has gone through initialization. Further detail regarding the operation of the skin grafting system 3000 is provided below.

Figure 5A:
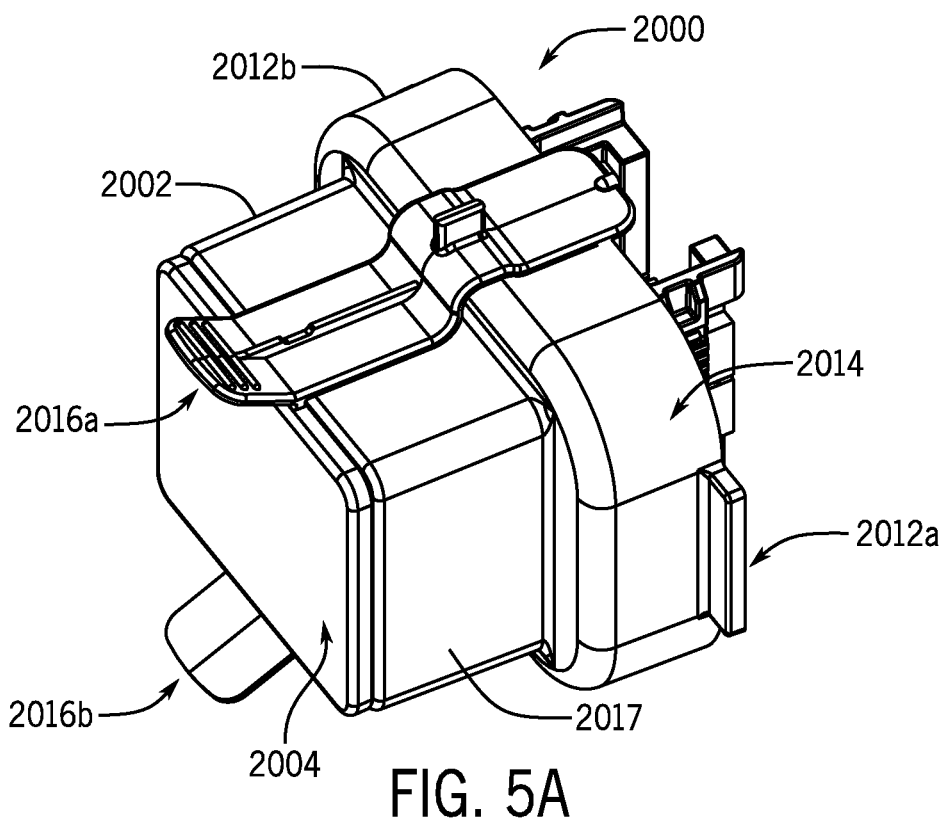
FIG. 5A is a perspective view of a cartridge assembly including a removable cover, in accordance with some implementations of the present disclosure.
Figure 5B:
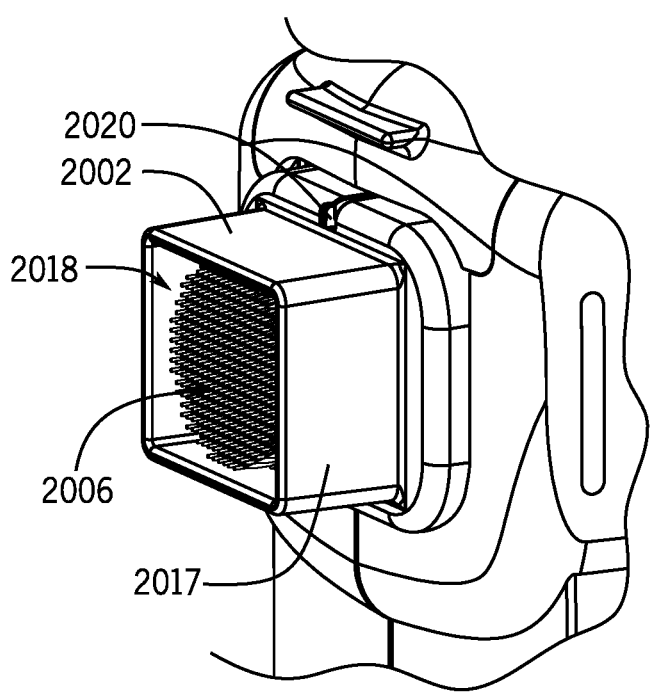
FIG. 5B is a perspective view of a cartridge corresponding to the cartridge of FIG. 5A, in accordance with some implementations of the present disclosure.

Referring now to FIGS. 5A-5B, the cartridge 2002 and a cartridge assembly 2000 are shown, according to some configurations. As shown, the cartridge assembly 2000 can include the cartridge 2002, and a cartridge cover 2004 that can be removably affixed to a microneedle chamber 2018. The microneedle chamber 2018 can enclose a plurality of microneedles 2006. In some configurations, the microneedles 2006 can be arranged as an array within the microneedle chamber 2018. As shown by FIG. 5A, the combination of the cartridge cover 2004 and the microneedle chamber 2018 can form an enclosure for the microneedles 2006. The cartridge cover 2004 can include release levers 2016a, 2016b, which can be simultaneously depressed by a user to remove the cartridge cover 2004 from the cartridge 2002. In some implementations, the cartridge cover 2004 can latch onto cartridge arms 2020, when the plurality of microneedles are in a specific position. The cartridge arms 2020 can prevent movement of the plurality of microneedles when the cartridge cover 2004 is affixed to the cartridge 2002.

In some configurations, the cartridge 2002 can include a tissue stabilizer 2014, which forms a peripheral housing 2017 and can be configured to stabilize tissue during harvesting. That is, the tissue stabilizer 2014 forms a peripheral housing 2017 that is wider than the microneedle chamber 2018, allowing for a greater distribution of force during use of the skin grafting system 3000 on tissue. As shown, the tissue stabilizer 2014 can further include loading tabs 2012a, 2012b that extend outwardly. In some configurations, the loading tabs 2012a, 2012b can slide into contact with the engagement slot 1002 during loading of the cartridge assembly 2000 into the loading aperture 1006.

Referring now to FIGS. 6A-6C, a microneedle 2050 and a microneedle array 2006 are shown, according to configurations of the present disclosure. The microneedle 2050 can facilitate harvesting of tissue from a donor site. In some configurations, the microneedle 2050 can include a hollow tube 2054 that can include a plurality of points 2056 at the distal end thereof. In some non-limiting examples, needle systems such as described in U.S. Pat. Nos. 9,060,803; 9,827,006; 9,895,162; and US Patent Application Publication Nos. 2015/0216545; 2016/0015416; 2018/0036029; 2018/0140316 and/or combinations or components thereof may be used.

In some configurations of the present disclosure, the hollow tube 2054 can be provided with two points 2056, and the points 2056 can be sufficiently angled for penetrating and cutting the biological tissue to remove small micrografts therefrom. Such a hollow tube 2054 can be provided with two points 2056, and a "narrow heel" portion positioned between the two points 2056. According to some embodiments, the narrow heel portion can be sharpened, such that a cutting edge corresponding to the hollow tube 2054 is created.

In some configurations, the hollow tube 2054 can be slideably attached to a substrate 2058, such that the hollow tube 2054 can pass through a hole provided in the substrate 2058, as shown in FIG. 6A. The position of the hollow tube 2054 relative to the substrate 2058 can be controlled by translating the hollow tube 2054 relative to the substrate 2058, e.g., substantially along the longitudinal axis of the hollow tube 2054. In this manner, the distance that the distal end of the hollow tube 2054 protrudes past the lower surface of the substrate 2058 can be controllably varied.

The microneedle 2050 can further include a pin 2052 provided in the central lumen or opening of the hollow tube 2054. The diameter of the pin 2052 can be substantially the same as the inner diameter of the hollow tube 2054 or slightly smaller, such that the hollow tube 2054 can be translated along an axis corresponding to pin 2052 while the pin 2052 fills or occludes most or all of the inner lumen of the hollow tube 2054. The pin 2052 can be formed of a low-friction material, or coated with a low-friction material such as, e.g., Teflon® or the like, to facilitate motion of the hollow tube 2054 with respect to the pin 2052 and/or inhibit accumulation or sticking of biological material to the pin 2052. The distal end of the pin 2052 can be substantially flat to facilitate displacement of a tissue micrograft within the hollow tube 2054, when the hollow tube 2054 is translated relative to the pin 2052.

The hollow tube 2054 can be translated relative to the pin 2052, e.g., substantially along the longitudinal axis of the hollow tube 2054. In this manner, the position of the distal end of the hollow tube 2054 relative to that of the distal end of the pin 2052 can be controllably varied. For example, the location of the distal ends of both the hollow tube 2054 and the pin 2052 relative to that of the lower surface of the substrate 2058 can be controllably and independently selected and varied.

FIG. 6B shows one configuration of the present disclosure, in which the pin 2052 can be positioned relative to the hollow tube 2054 such that their distal ends are substantially aligned. In another configuration, the pin 2052 can extend slightly beyond the distal end of the hollow tube 2054, such that sharpened portions of the hollow tube 2054 can be shielded from undesired contact with objects and/or users. Portions of the pin 2052 and/or hollow tube 2054 can optionally be provided with a coating or surface treatment to reduce friction between them and/or between either component or biological tissue.

As described herein, a plurality of microneedles (e.g., microneedle 2050) can form a microneedle array 2006. FIG. 6C shows a top view of an exemplary microneedle array 2006, according to configurations of the present disclosure. In some configurations, the microneedle array 2006 can be substantially circular. The microneedle array 2006 can be formed by assembling a plurality of rows of needles, either horizontal or vertical rows. This design can be modular, and the configuration can take on any shape or size using various size rows as modules. In some configurations, all of the microneedles can be actuated, e.g., inserted into the tissue, simultaneously. In other configurations, groups or sections can be actuated sequentially. For example, the microneedle array 2006 can be divided into quadrants and each quadrant can be sequentially actuated. Sequentially can refer to actuating each row in a linear order, (e.g., row1, row2, row3), or non-linear (e.g. row1, row10, row3). Or, each row of microneedles can be separately and sequentially actuated. Additionally, each single microneedle can be separately and sequentially actuated. In some configurations, one row can be actuated at a time, e.g., 20 rows can be individually actuated in sequence, while in other configurations, two, three, four or more rows can be actuated at a time. An advantage to sequentially actuating segments of the microneedle array 2006 is that insertion of a segment can require less force on the donor site than insertion of the entire microneedle array 2006. In some configurations, the microneedle array 2006 can be driven using a solenoid (e.g., solenoid 1052). Multiple actuations using the solenoid can sequence the insertion row by row.

Figure 7:
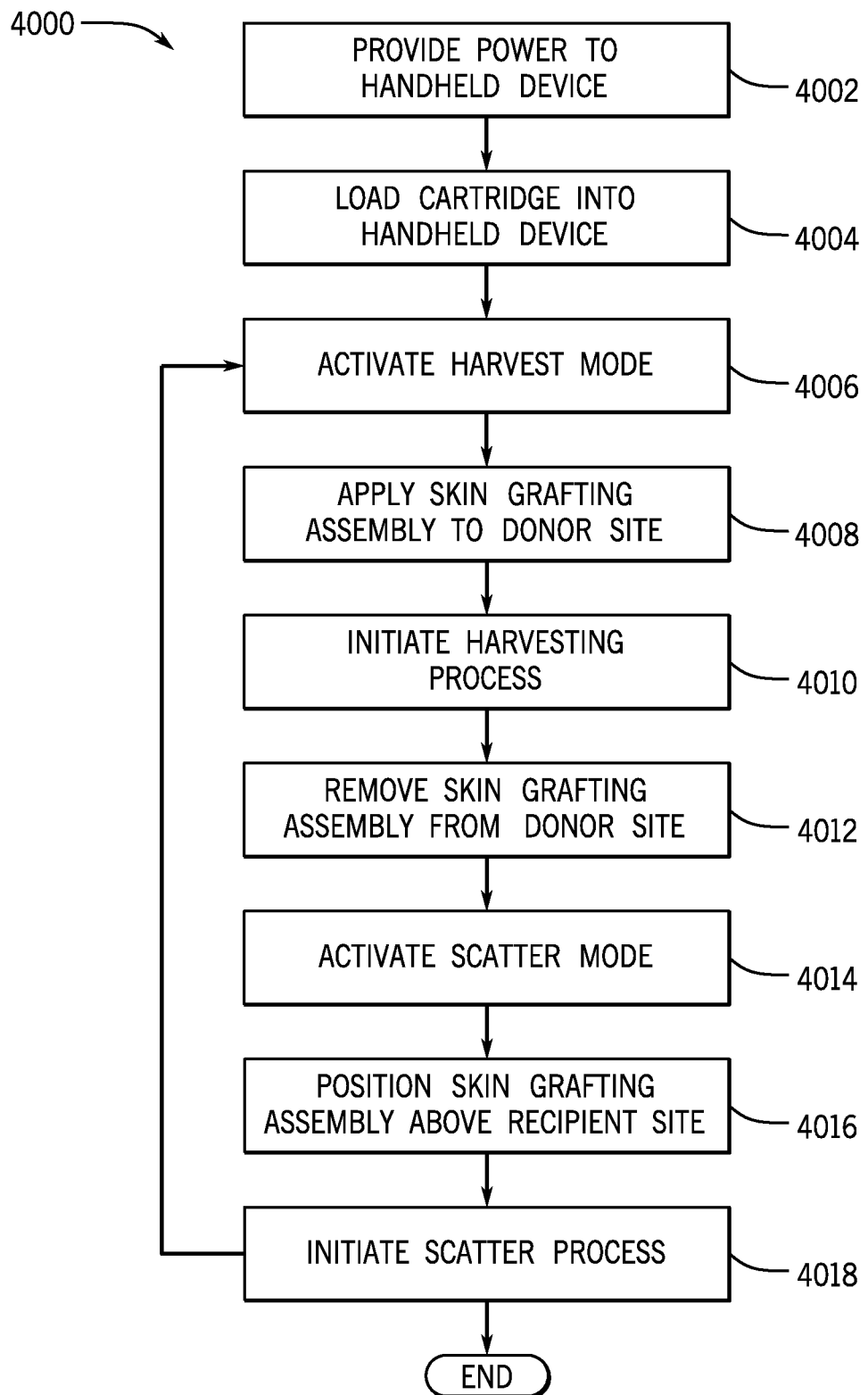
FIG. 7 is a procedural flowchart illustrating a method of harvesting and scattering tissue, in accordance with some implementations of the present disclosure.

Referring now to FIG. 7, some non-limiting examples of steps of a process 4000 for harvesting and scattering tissue is shown, according to configurations of the present disclosure. In some configurations, the process 4000 can be implemented using the skin grafting system 3000, as described above. As shown, the process 4000 includes providing power to the handheld device (process block 4002). In some configurations, the handheld device can be the same or similar to handheld device 1000. The process 4000 is shown to further include loading a cartridge into the handheld device (process block 4004). In some configurations, the cartridge can be the same or similar to cartridge 2002, or cartridge assembly 2000. Further, the process 4000 is shown to include activating a harvest mode (process block 4006). This activation can be initiated via user interface 1008, according to some configurations, such as will be described. Alternatively, the activation can be initiated via contact with a donor site. The process 4000 is shown to include applying a skin grafting system (e.g., skin grafting system 3000) to a donor site (process block 4008). The donor site can correspond to a healthy area of tissue on a patient. Next, the process 4000 is shown to include initiating a harvesting process (process block 4010). In some configurations, this initiation can occur via the above-described trigger 1014. The process 4000 is shown to further include removing the skin grafting system from the donor site (process block 4012). Next, the process 4000 is shown to include activating a scatter mode (process block 4014). In some configurations, this activation can occur via user interface 1008, such as will be described. The process 4000 is shown to further include positioning the skin grafting system above a recipient site (process block 4016). In some configurations, the recipient site can correspond to a damaged area of tissue on the patient. Next, the process 4000 is shown to include initiating a scatter process (process block 4018). In some configurations, this initiation can occur via actuation of the above-described trigger 1014. As shown, the process 4000 can end after the scatter process (process block 4018), or can return to process block 4006 to reactivate the harvest mode. In some configurations, a single cartridge (e.g., cartridge 2002) can be used multiple times on the same patient. Advantageously, if the recipient site is relatively large, multiple harvests and scatters can occur using a single cartridge. Accordingly, the process 4000 can continue with process blocks 4006 through 4018 until a user is ready to dispose of the cartridge.

According to configurations of the present disclosure, the harvest process and scatter process can be performed using skin grafting system 3000. A non-limiting description of the internal functions of the handheld device 1000 and cartridge 2002 are accordingly disclosed herein.

User Interface

Referring to FIG. 2B, as one non-limiting example, an example of using the user interface 1008 to control the above-described process is provided. Upon providing power to the handheld device, the stand-by input 1018 can flash green when the handheld device 1000 first powers on (e.g., for ~8 seconds at initial start-up). This can inform the user that the handheld device 1000 is performing a start-up self-test or other operation. As another non-limiting example, the stand-by input 1018 can produce steady green illumination when the handheld device 1000 is on and ready for subsequent use. In some configurations, pressing the stand-by input 1018 for a pre-determined amount of time (e.g., 3 seconds, 5 seconds, or the like) can cause the handheld device 1000 to enter a stand-by mode. Continuing with the non-limiting example, the stand-by input 1018 can stop producing light when the handheld device 1000 is in stand-by mode. Other light colors, patterns, and timing can be implemented, according to various configurations and preferences.

As another non-limiting example, the indicator light 1020 can produce steady white light when the handheld device 1000 is in harvest mode but sufficient pressure against a donor site has not been achieved, such as will be described during a skin grafting process. Further, the indicator light 1020 can produce steady green light when the handheld device 1000 is in harvest mode and sufficient pressure against the donor site has been achieved (and the trigger 1014 is disengaged). The indicator light 1020 can produce flashing green light when the handheld device 1000 is in the process of harvesting. If pressure drops below a threshold value during the harvesting process, the indicator light 1020 can produce flashing white light. Further, the indicator light 1020 can produce flashing white light when the handheld device 1000 is experiencing a fault condition.

In another non-limiting example, the scatter input 1022 can produce steady white light when the harvest process is complete. In some configurations, a subsequent press of the scatter input 1022 can cause the handheld device 1000 to enter a scatter mode. The scatter input 1022 can produce steady green light when the handheld device 1000 is in scatter mode. Similar to the indicator light 1020, the scatter input 1022 can produce flashing white light when the handheld device 1000 is experiencing a fault condition. In some configurations, the scatter input 1022 can produce flashing white light during the harvesting process, which can indicate that extraction recovery is needed. A subsequent press of the scatter input 1022 can activate an extraction recovery process. Once the extraction recovery process is complete, the scatter input 1022 can produce a steady white light. A detailed description of the extraction recovery process is provided below.

In some configurations, similar to the indicator light 1020, the indicator light 1016 can produce a solid green light when the handheld device 1000 is in the harvest mode and sufficient pressure against the donor site has been achieved (and the trigger 1014 is disengaged). Additionally, the indicator light 1020 can produce flashing green light during the harvesting process, according to some configurations.

Skin Grafting System Operating Positions

In some configurations, a plurality of operating positions corresponding to the skin grafting system 3000 can be defined. Notably, the skin grafting system 3000 can operate using additional operating positions not explicitly defined.

Some configurations of the present disclosure include a horizontal carriage home position, where the horizontal carriage assembly 1082 can be in a position that occludes the horizontal flag sensor 1064. This position can be a "safe" position that keeps the carriage away from other moving parts.

Some configurations of the present disclosure include a vertical carriage home position, corresponding to a calibrated position where the vertical carriage assembly 1108 can be aligned with the corresponding components for loading or for harvesting. This position can be below the vertical flag sensor occlusion point. From a user's perspective, it can appear that the vertical carriage assembly 1108 is closest to the engagement slot 1002 of the handheld device 1000.

Some configurations of the present disclosure include a vertical carriage unlock/scatter position corresponding to a calibrated position where the vertical carriage assembly 1108 has unlocked the needle retract slide 1110 by pushing the needle retract slide latches 1116a, 1116b over their respective unlock cams 1102a, 1102b. This can be the highest position the vertical carriage assembly 1108 will travel to. From a user's perspective, it can appear that the vertical carriage assembly 1108 is up inside the handheld device 1000.

Some configurations of the present disclosure include a "flipper in" position and a "flipper out" position. Each flipper 1074 can have two defined positions that the handheld device 1000 detects via flag sensors that can provide positive feedback that each position has been reached. The "flipper in," or retracted, position can correspond to when the flipper 1074 is safely away from moving parts. The "flipper out," or extended, position can correspond to when the flipper 1074 is blocking the top plate 1112. The "flipper out" position can be used for initialization, when the needle retract slide 1110 (and therefore the cartridge 2002) is locked.

Some configurations of the present disclosure include a vertical carriage lock position, corresponding to a calibrated position where the vertical carriage assembly 1108 can move to (with the flippers 1074 extended out) to compress the needle retract springs 1120 and to lock the needle retract slide latches 1116. This "locking" is what can allow the needles to later be retracted, while also locking the cartridge 2002 inside the handheld device 1000.

Some configurations of the present disclosure include a vertical carriage lock relax position, which can be a position that is offset from a calibrated lock position, where a properly locked needle retract slide top plate 1112 will no longer be putting pressure on the flippers 1074, and therefore the flippers 1074 can be safe to retract in. Conversely, if the needle retract slide top plate 1112 is not properly locked, this position can be designed to maintain enough pressure on the flippers 1074 so that they will not retract in. This position can enable the handheld device 1000 to positively sense a proper locking of the needle retract slide 1110.

Some configurations of the present disclosure include a vertical carriage extract position, which can be a position that is offset from a calibrated unlock position, where the needle retract slide 1110 will not be unlocked and the extended needles can be behind the tissue stabilizer 2014. After harvest, this position is where the vertical carriage assembly 1108 can go to extract the needles (containing the tissue grafts) from the tissue prior to scattering. Advantageously, tissue grafts may not be exposed in this position, as the needles remain extended.

Some configurations of the present disclosure include a harvest recovery mode, which can occur during the harvest process. The harvest recovery mode can include attempting to continue deploying the needle modules into the tissue. Additionally, the harvest recovery mode can be automatic and fully controlled by on-board software (i.e., no user interaction required). In some embodiments, the harvest recovery mode can include reversing the motion of the horizontal carriage assembly 1082 by a predetermined distance or time interval. Subsequently, the horizontal carriage assembly 1082 can advance and again attempt to deploy the needle modules into the tissue.

Some configurations of the present disclosure include an extraction recovery mode, which can occur after the needles have been deployed (and the handheld device 1000 is attempting to return the horizontal carriage to its home position). In some configurations, it may be possible for the horizontal carriage assembly 1082 to get stuck due to increased friction from the needle modules. If this occurs, the handheld device 1000 can blink the scatter light (on the scatter input 1022) white, indicating that an extraction recovery is needed. The user may then relieve the downward force on the tissue, and press the scatter input 1022, which will allow the handheld device 1000 to continue with extracting the needles from the tissue.

Skin Grafting Assembly Vertical Operation

Various components corresponding to the handheld device 1000 and cartridge 2002 can have a predefined operation based on the current mode of the handheld device 1000 (e.g., initialization, harvest mode, scatter mode, etc.), according to some configurations.

In some configurations, the vertical component assembly 1046 can have a predefined "loading" configuration that corresponds to loading of the cartridge 2002 into the handheld device 1000. During loading, for example, the solenoid plunger bar 1106, each flipper 1074, and the needle retract slide 1110 can be retracted (the needles retracted). The vertical carriage assembly 1108 can be set to the home position (as described above).

In some configurations, the vertical component assembly 1046 can have a predefined "initialization" configuration. During initialization, for example, each flipper 1074 can be extended (flipper out), and the needle retract slide 1110 can be locked with the needle retract springs 1120 loaded (the needles remain retracted). The vertical carriage assembly 1108 can be set to the lock position (see above). With each flipper 1074 extended, the vertical carriage assembly 1108 can move up to the lock position. The extended flippers 1074 can hold the needle retract slide 1110 in place. When the vertical carriage assembly 1108 reaches the lock position, the needle retract slide latches 1116 can lock the top plate 1112 in place with the needle retract springs 1120 loaded. In some configurations, this does not move the needles from their retracted state.

In some configurations, the vertical component assembly 1046 can have a predefined "initialized" configuration, which can correspond to the skin grafting system 3000 being ready to harvest. During the initialized configuration, for example, each flipper 1074 can be retracted (flipper in), and the needle retract slide 1110 can be locked with the needle retract springs 1120 loaded. In some configurations, this does not move the needles from their retracted state. The vertical carriage assembly 1108 can move back down to the home position, according to some configurations.

In some configurations, the vertical component assembly 1046 can have a predefined "harvest" configuration corresponding to an applied user force. During the harvest configuration, for example, the needle retract slide 1110 can remain locked with the needle retract springs 1120 loaded and the needles retracted. The vertical carriage assembly 1108 can remain in the harvest position, according to some configurations. When the user positions the skin grafting system 3000 at the donor site and applies downward force, the user will detect the tissue stabilizer 2014 moving a small amount in the direction opposite to the applied force, causing the indicator lights 1016 and 1020 to light up, indicating to the user that there exists proper alignment for harvest. In some configurations, the indicator light 1016 can illuminate green, to provide a visual confirmation of force to the user.

In some configurations, the vertical component assembly 1046 can have a predefined "harvest" configuration corresponding to needle deployment. During this harvest configuration, for example, the solenoid plunger bar 1106 can advance, and the needle retract slide 1110 can remain locked with the needle retract springs 1120 loaded. Notably, the needles (e.g., from microneedle array 2006) can be deployed into the tissue. The vertical carriage assembly 1108 can remain at the home position, and a user force can still be applied via the handheld device 1000, according to some configurations. When the user pulls the trigger 1014, the skin grafting assembly 3000 can begin the harvest sequence. Accordingly, the skin graft assembly 3000 can advance each microneedle array row of needles into the tissue by hitting the hammers 1098a, 1098b with the solenoid plunger bar 1106.

In some configurations, the vertical component assembly 1046 can have a predefined "extraction" configuration. During the extraction configuration, for example, the solenoid plunger bar 1106 can be retracted, the needle retract slide 1110 can remain locked with the needle retract springs 1120 loaded. The needles (e.g., from microneedle array 2006) can remain deployed into the tissue at the start of extraction. The vertical carriage assembly 1108 can move to the extraction position (described above). In some configurations, after the harvest is complete, the skin grafting system 3000 can extract the needles by lifting all of needles within the microneedle array 2006 at once. The needles can be lifted up to the extraction position, and the user force can be removed. In some configurations, the needles can remain advanced relative to the pins (e.g., pin 2052) and the tissue stabilizer 2014 can remain stationary when the needles are retracted.

In some configurations, the vertical component assembly 1046 can have a predefined "scatter" configuration. During the scatter configuration, for example, the needle retract slide 1110 can be in a retracted position, with the needles similarly retracted. In some configurations, the vertical carriage assembly 1108 can move from the extracted position. When the user activates the scatter sequence, the skin grafting system 3000 can move the vertical carriage assembly 1108 from the extracted position, which can release the loaded needle retract springs 1120, and the needle retract slide 1110. Accordingly, this movement can retract the needles relative to the pins (e.g., pin 2052), thus exposing the grafts and positioning the components for a scatter sequence.

In some configurations, the vertical component assembly 1046 can have a "scatter" configuration corresponding to an advanced needle position. During this scatter configuration, for example, the solenoid plunger bar 1106 can advance, and the needle retract slide 1110 can advance (similarly, the needles can advance). According to some configurations, the solenoid plunger bar 1106 can advance, first hitting the top plate 1112, and then hitting the needle modules (e.g., within microneedle array 2006). This can push the top plate 1112 ahead of needle carriers, thus preventing damage to the carriers. The advancing of the needles, followed by the rapid retraction of those needles (by the unlocked top plate 1112) can disperse the grafts into the recipient site.

Power on Self-Test

In some configurations, the handheld device 1000 can perform a self-test upon start-up (e.g., when the handheld device 1000 is first powered on). In some configurations, the self-test can occur when the handheld device 100 is plugged in to receive power, and the stand-by input 1018 is pressed and released. The stand-by input 1018 can flash green throughout the duration of the self-test, according to some configurations. Next, the horizontal carriage assembly 1082 can move a very small amount forward, such that the horizontal flag sensor 1064 is cleared. Subsequently, the horizontal carriage assembly 1082 can return to the home position.

During the self-test, the vertical carriage assembly 1108 can move a very small amount upwards, such that the vertical flag 1118 clears the sensor. Subsequently, the vertical carriage assembly 1108 can return to the home position. In some configurations, the vertical carriage assembly 1108 can move up to the unlock position, where it can move the needle retract slide latches 1116, before returning to the home position. This can, for example, release the needle retract slide 1110, in the event that it is locked (e.g., cartridge 2002 is locked in).

In some configurations, the horizontal carriage assembly 1082 can move to a predetermined position (e.g., approximately two-thirds of the way through its full range), which can verify that a cartridge (e.g., cartridge 2002) is not present. Subsequently, the horizontal carriage assembly 1082 can return to the home position.

During the self-test, the flippers 1074 can extend out and then retract back in. Further, in some configurations, some or all lights on handheld device 1000 can flash (e.g., indicator light 1016, 1020, scatter input 1022, etc.). Upon completion of the self-test, the stand-by input 1018 can light up solid green, for example, which can indicate that the self-test was successful.

Cartridge Loading and Initialization

In some configurations, the skin grafting system 3000 can have a predefined cartridge loading and initialization process. The user can open the loading door 1004, then slide the cartridge assembly 2000 (i.e., including the cartridge cover 2004) into the engagement slot 1002. The cartridge latch 1114 can lock onto the cartridge 2002. The user can then remove the cartridge cover 2004 and close the loading door 1004, which can activate the internal loading door switch.

The initialization process can further include moving the horizontal carriage assembly 1082 from the home position, such that it can detect the cartridge presence by stalling on the first cartridge segment. Subsequently, the horizontal carriage assembly 1082 can return to the home position. Additionally, the vertical carriage assembly 1108 can move a small amount, such that the vertical flag 1118 clears the sensor, and then the vertical carriage assembly 1108 can return to the home position.

In some configurations, the flippers 1074 can extend out above the top plate 1112. The vertical carriage assembly 1108 can move to the lock position. While moving to the lock position, the flippers 1074 can hold the top plate 1112 in place while the needle retract slide latches 1116 move out, and eventually lock over the top plate 1112. Accordingly, the needle retract springs 1120 can be held in a compressed state. While this is happening, for example, the lockdown latches 1126 can spring out under the needle segments (e.g., within the microneedle array 2006), in preparation for locking the needle segments down during the harvest sequence. In some configurations, the vertical carriage assembly can then move a small amount down, thus moving into the lock relax position (described above). Additionally, the flippers 1074 can retract back in.

The initialization process can further include returning the vertical carriage assembly 1108 to the harvest position. The horizontal carriage assembly 1082 can engage with the first needle segment (within microneedle array 2006) by stalling against the segment and subsequently backing off by a small predetermined distance. The handheld device 1000 can then calculate the position of each needle segment. Upon completion of the initialization process, the indicator light 1020 can illuminate white to indicate that the handheld device 1000 is ready for the harvest sequence.

Methods of Harvest and Extraction

In some configurations, a user can harvest and extract tissue columns using a harvesting process. The user can position the handheld device 1000 at the donor site, with the tissue stabilizer 2014 pressed against the skin. The user can use one or two hands to apply force against the skin via the handheld device 1000. The tissue stabilizer interface components can move upward, compressing the position sensing springs 1056 until the position sensing flag 1062 occludes the flag sensor. In some configurations, the indicator lights 1016, 1020 can illuminate green, thus indicating that the trigger 1014 is active.

Once the trigger 1014 is active, the user can pull the trigger 1014 (while maintaining the force on the skin) and the handheld device 1000 can begin the harvest sequence. In some configurations, the indicator lights 1016, 1020 can blink green throughout the duration of the harvest and the extraction. The position sensing flag 1062 can be monitored throughout the harvest (between solenoid activations) to ensure that sufficient force is maintained. The solenoid 1052 can rapidly advance the solenoid plunger bar 1106, which can advance the two hammers 1098*a*, 1098*b*, and insert the first needle module into the tissue. The needle module travels past the needle module lockdown latches as it is inserted. Subsequently, the solenoid 1052 and hammers 1098*a*, 1098*b* can retract, and the needle segment can remain locked down in the tissue.

In some configurations, the horizontal carriage assembly 1082 can advance to the calculated position of the next needle segment. Alternatively, the position of the next needle segment can be recalculated or otherwise reverified throughout the harvest process. The solenoid 1052 can rapidly advance the solenoid plunger bar 1106, which can advance the two hammers 1098*a*, 1098*b*, and insert the next needle module into the tissue. The needle module can travel past the lockdown latches 1126 as it is inserted. The lockdown latches 1126 can spring back out, and the solenoid 1052 and hammers 1098*a*, 1098*b* can retract. This insertion process can repeat until all needle segments have been inserted into the tissue.

After completing the insertion of all segments, the horizontal carriage assembly 1082 can return to the home position, according to some configurations. The vertical carriage assembly 1108 can move up to the extraction position, extracting the needles from the tissue, and positioning the needles safely up inside the tissue stabilizer 2014. The indicator lights 1016, 1020 can stop blinking green and turn off. Additionally, the scatter input 1022 can be illuminated white, indicating that the handheld device 1000 is ready to proceed with the scattering process. Upon completion of the harvesting process, the user can remove the force on the tissue, and lift the handheld device 1000 away.

Methods of Scatter

In some configurations, a user can scatter the tissue columns after the harvesting process. Once the user has removed the handheld device 1000 from the donor site (with the tissue columns harvested), the needles can be safely up inside of the cartridge 2002 (e.g., within the tissue stabilizer 2014). With the recipient site ready for the tissue columns, the user can activate the scatter mode by pressing the scatter input 1022. In some configurations, the scatter input 1022 can change from being illuminated white to green.

In some configurations, the user can position the cartridge 2002 directly above the recipient site. The user can then pull the trigger 1014 and the vertical carriage assembly 1108 can move out of the extract position, which can release the needle retract slide 1110 and retract the needles behind the pins (e.g., pins 2052). The handheld device 1000 can rapidly advance the solenoid plunger bar 1106 which accordingly push both the needle retract slide 1110 and the needle modules. The needle retract slide 1110 can remain pushed ahead of the needle modules to prevent damage to the needle modules. Subsequently, the solenoid plunger bar 1106 can retract, which can cause the needle retract slide 1110 to retract (pulling the needle modules back with the needle retract slide 1110). The process of rapidly advancing the solenoid plunger bar 1106 can be repeated several times, which can ensure that as many grafts as possible have been deposited into the recipient site. In some configurations, six activations of the solenoid 1052 can occur. After the scatter process has completed, the vertical carriage assembly 1108 can return to the home position, with the needle retract slide 1110 unlocked.

Cartridge Removal

In some configurations, once the user has completed the harvest and scatter processes, the user can open the loading door 1004, depress the cartridge latch 1114, and slide the cartridge 2002 out. In some configurations, if the user wants to complete another harvest with the same cartridge 2002, the user can open and close the loading door 1004 (i.e., without removing the cartridge 2002). This can begin another initialization process via the handheld device 1000. Alternatively, the user can begin another initialization process via an input (not shown) on the user interface 1008.

Fluid Ingress Protection

As described above, the cartridge 2002 can be used for multiple harvest and scatter processes (on a single patient), before removal from the handheld device 1000 and subsequent disposal. In some situations, repeated tissue punctures via the microneedle array 2006 can cause localized bleeding. Further, the repeated deployment and retraction of the needle modules can result in the dispersion of blood. Since the cartridge 2002 can be disposable, blood dispersion onto, for example, the exterior of the microneedle chamber 2018 may be inconsequential. However, the handheld device 1000 can be reusable. Accordingly, it may be advantageous to prevent blood ingress into housing 1036. As an example, should blood penetrate the housing 1036, an extensive cleaning and disinfecting process may be required.

The present disclosure includes systems and methods for preventing blood ingress. In particular, the present disclosure provides a clinical soil control system that can prevent fluid ingress into the handheld device 1000 (e.g., via the housing 1036), and/or general fluid exposure to the reusable handheld device 1000 (e.g., the exterior of the housing 1036). In some implementations, the clinical soil control system can protect the contact point that occurs between the engagement slot 1002 and the cartridge 2002 (see, e.g., FIG. 1). Additionally, the clinical soil control system of the present disclosure can be designed to protect the contact point that occurs between the loading door 1004 and the cartridge 2002 (see, e.g., FIG. 1). In some configurations, the clinical soil control system can include an absorptive material to further prevent fluid ingress onto and/or into the housing 1036.

Figure 8A:
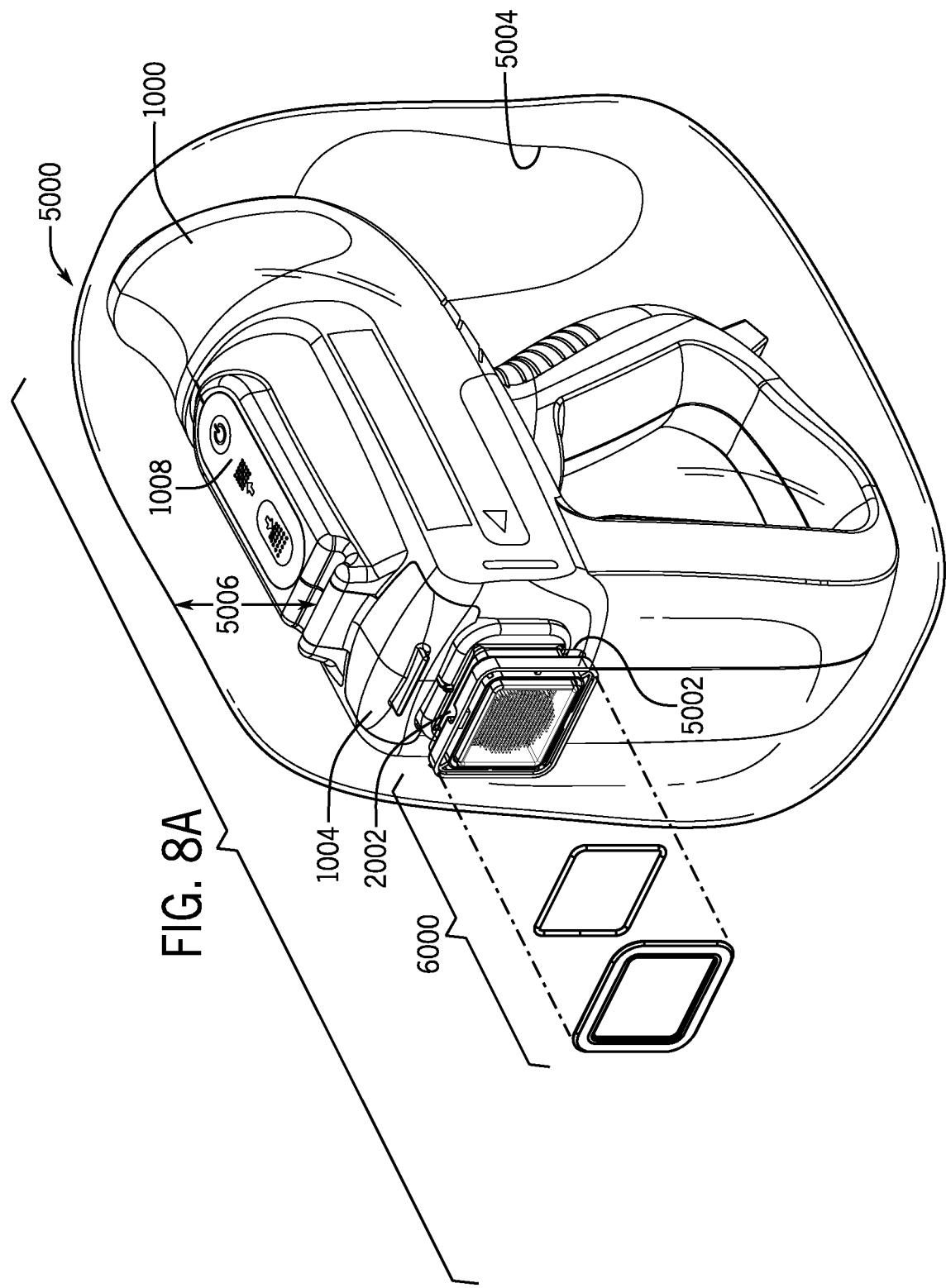
FIG. 8A is a perspective view of a clinical soil control system, in accordance with some implementations of the present disclosure.
Figure 8B:
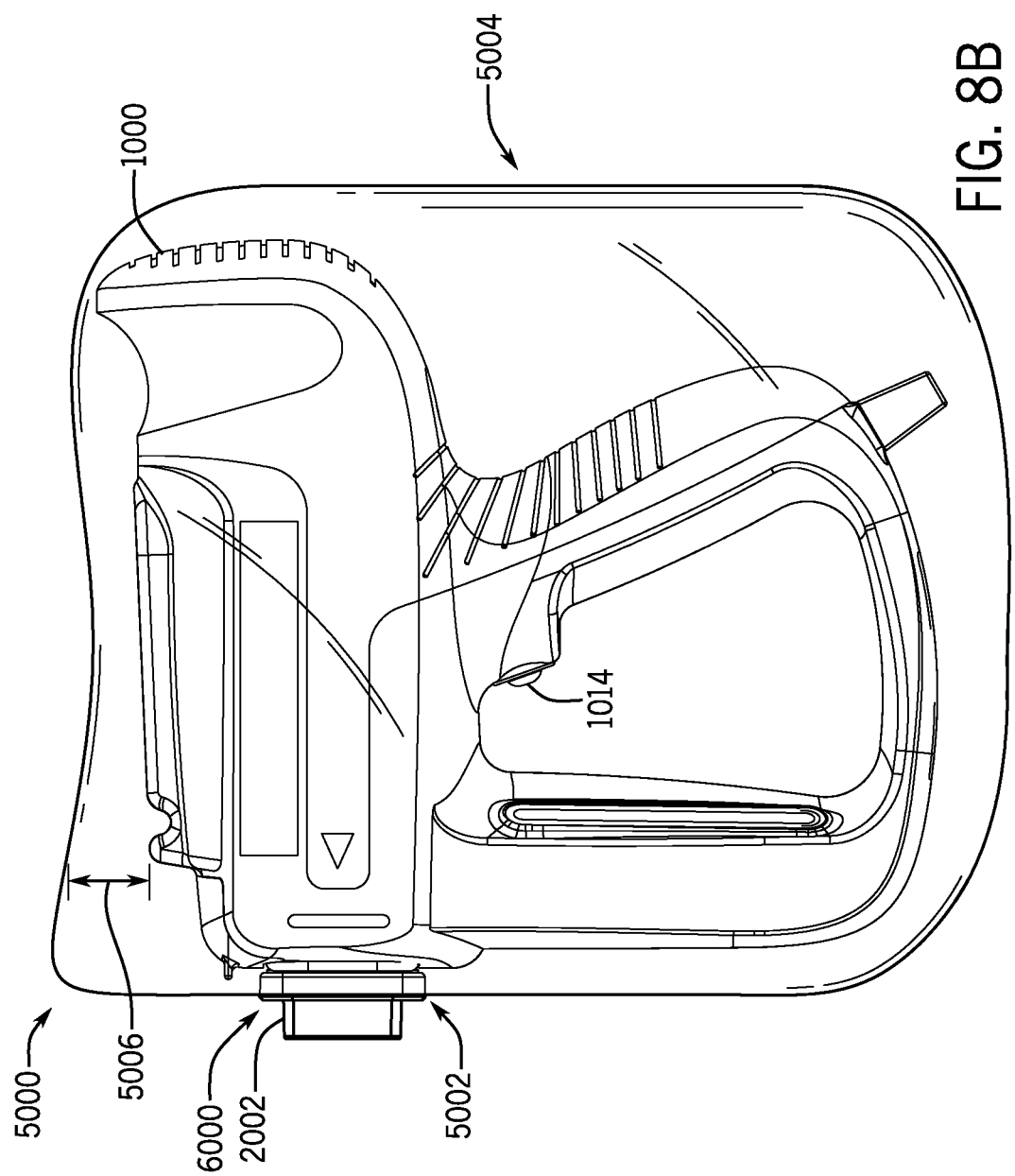
FIG. 8B is a side view of the clinical soil control system of FIG. 8A, in accordance with some implementations of the present disclosure.

Referring now to FIGS. 8A-8B, a clinical soil control system is shown, according to some implementations of the present disclosure. In general, the clinical soil control system can include a cincture (e.g., a gasket assembly 6000), a device cover 5000, and an absorptive material 8000 (see, e.g., FIG. 15A). In some configurations, the clinical soil control system can include one of, or various combinations of: the cincture (e.g, the gasket assembly 6000), the device cover 5000, and the absorptive material 8000.

As shown by FIGS. 8A-9B, a clinical soil control system can include the device cover 5000. The device cover 5000 can cover a portion of the handheld device 1000, or alternatively, the entirety of the handheld device 1000. In some configurations, the device cover 5000 can include one or more openings which may facilitate access to the handheld device 1000 and cartridge 2002 during a skin grafting process. As shown in FIG. 8A, as an example, the cartridge 2002 can extend through a cartridge opening 5002 in the device cover 5000. In this way, the cartridge 2002 can make contact with a patient (e.g., a donor site), while preventing clinical soil from contacting the handheld device 1000. As mentioned above, the cartridge 2002 can be disposable (i.e., discarded after use with a single patient), whereas the handheld device 1000 can be reusable (i.e., used for more than one patient).

In some implementations, the device cover 5000 can be substantially transparent. As an example, the device cover 5000 may include polyethylene film having a thickness within the range 0.01 mm to 0.5 mm, or alternatively 0.06 mm to 0.09 mm, which can allow a user to see through the device cover 5000. As another example, the device cover 5000 may include thermoplastic polyurethane having a thickness of about 0.7 mm, or within the range of 0.1 mm to 2.0 mm, or alternatively 0.6 mm to 0.8 mm, which can also allow a user to see through the device cover 5000. Broadly, the thickness range of the polyethylene film and/or the thermoplastic polyurethane can be any value that results in a flexible material membrane.

In some implementations, the device cover 5000 can be a flexible polymer sheet. The flexible polymer sheet can, in some implementations, be continuous. The device cover 5000 can also be a variety of other colors, e.g. white, black, blue, etc. In particular, the color of device cover 5000 can be selected to visually emphasize the location of any fluids that may have contacted the device cover 5000. For example, the device cover 5000 could be a substantially transparent or translucent white, blue, yellow, or other color that contrasts with dark red blood so as to highlight the location of blood that may have contacted the device cover 5000.

The device cover 5000 can include an access opening 5004, such as the access opening 5004 shown in FIGS. 8A-9B. The access opening 5004 can be sized such that a user can hold the handheld device 1000, and interact with corresponding elements (e.g., the user interface 1008, the trigger 1014, the loading door 1004, etc.) during a skin grafting process. Additionally, in some configurations, the access opening 5004 can be sized to receive the handheld device 1000 into an interior volume 5006 of the device cover 5000. The interior volume 5006 can be further sized to allow a user to interact with elements of the handheld device 1000 during a skin grafting process. As one example, the interior volume 5006 can accommodate the opening and closing of the loading door 1004, which can begin the initialization process described above. As another example, the interior volume 5006 can accommodate user interaction with the user interface device 1000.

As shown in FIG. 8A, the cartridge opening 5002 can be in contact with a cincture (e.g., the gasket assembly 6000). In general, the gasket assembly 6000 can be affixed to a perimeter of the cartridge opening 5002, and can contact outer portions of the cartridge 2002. The gasket assembly 6000 is discussed in greater detail with respect to FIGS. 10-13B below.

Figure 9A:
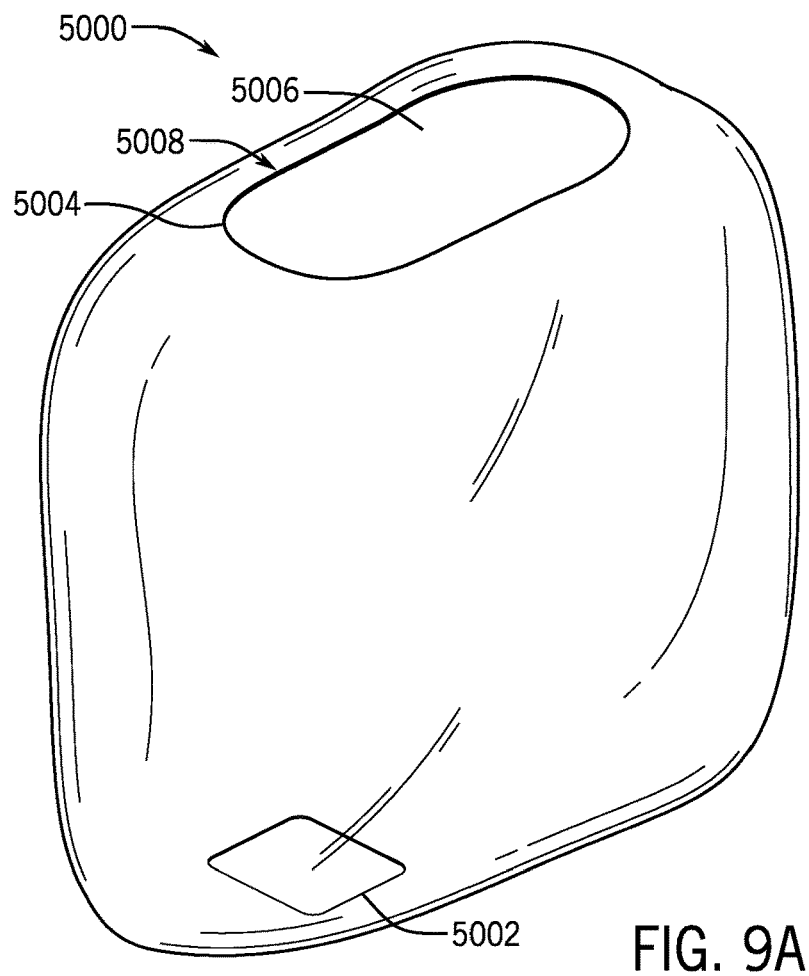
FIG. 9A is a perspective view of a device cover corresponding to a clinical soil control system, in accordance with some implementations of the present disclosure.
Figure 9B:
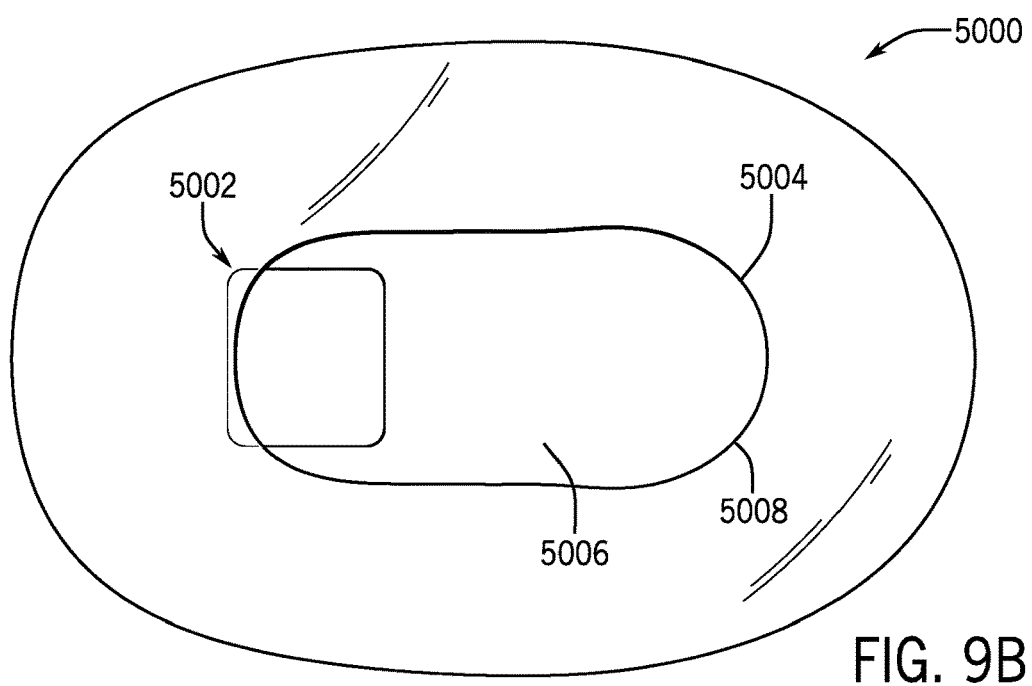
FIG. 9B is a top view of the device cover of FIG. 9A, in accordance with some implementations of the present disclosure.

Referring specifically to FIGS. 9A-9B, the device cover 5000 is shown, according to some implementations of the present disclosure. As shown, the access opening 5004 can include a means for restricting the size of the access opening 5004. As an example, the FIGS. 9A-9B are shown to include an elastic band 5008 as a means for restricting the size of the access opening 5004. The elastic band 5008 can stretch to accommodate the insertion of the handheld device 1000 into the interior volume 5006. Conversely, the elastic band 5008 can contract to decrease the size of the access opening 5004 such that a user can still grasp the handheld device 1000 through the access opening 5004, but the smaller opening prevents clinical soil from entering the interior volume 5006 during a skin grafting process. The elastic band 5008 can be sewn along the perimeter of the access opening 5004, or alternatively, can be attached via adhesive. In other implementations, the means for restriction can include a drawstring attached to portions of the access opening 5004. The drawstring can be tightened and loosened as desired by a user, and can decrease the access opening 5004 to prevent clinical soil ingress.

Referring generally to FIGS. 10-13C, a cincture (e.g., the gasket assembly 6000) is shown, according to implementations of the present disclosure. The gasket assembly can prevent clinical soil from contacting the handheld device by way of the cartridge opening 5002. According to some implementations, the gasket assembly 6000 can include a gasket case bottom 6002, a gasket 6004, and a gasket case top 6006 (see, e.g., FIG. 10). As shown, the gasket 6004 can be positioned between the gasket case bottom 6002 and the gasket case top 6006. According to some implementations, the gasket 6004 can be affixed to the gasket case bottom 6002 with, for example, adhesive. Similarly, the gasket case bottom 6002 and the gasket case top 6006 can be joined together via adhesive and/or internal engagement portions.

Figure 11A:
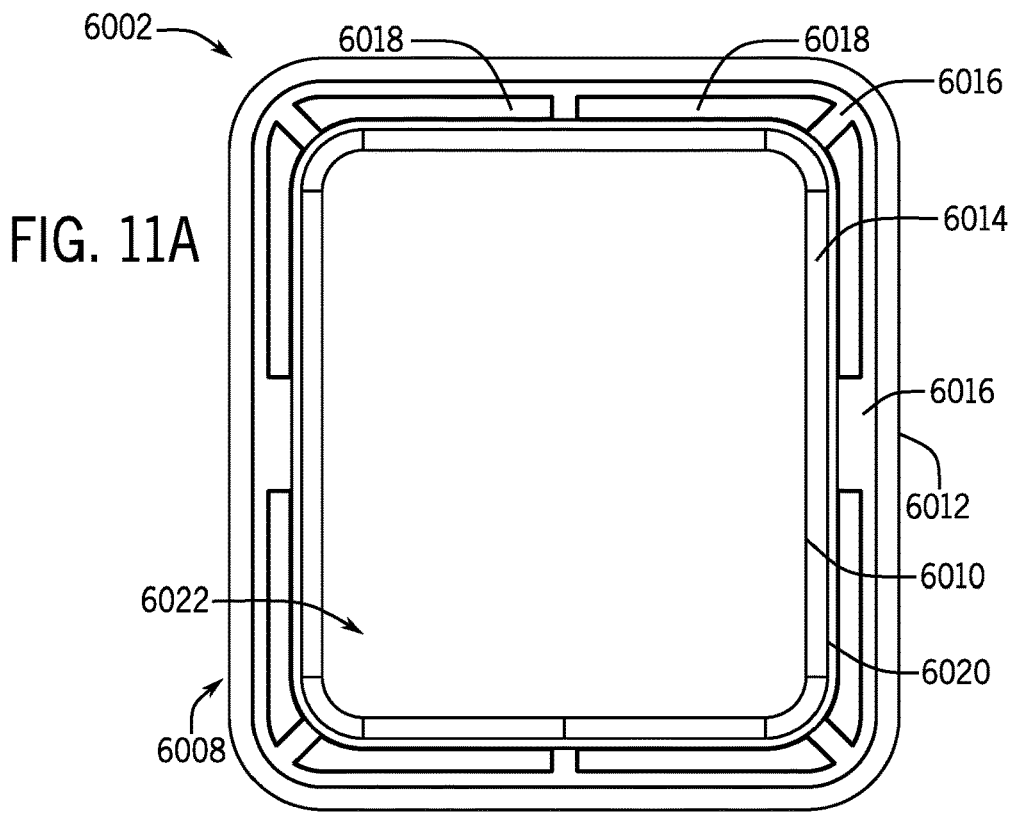
FIG. 11A is a front view of a gasket case bottom corresponding to a gasket enclosure, in accordance with some implementations of the present disclosure.
Figures 11B, 11C:
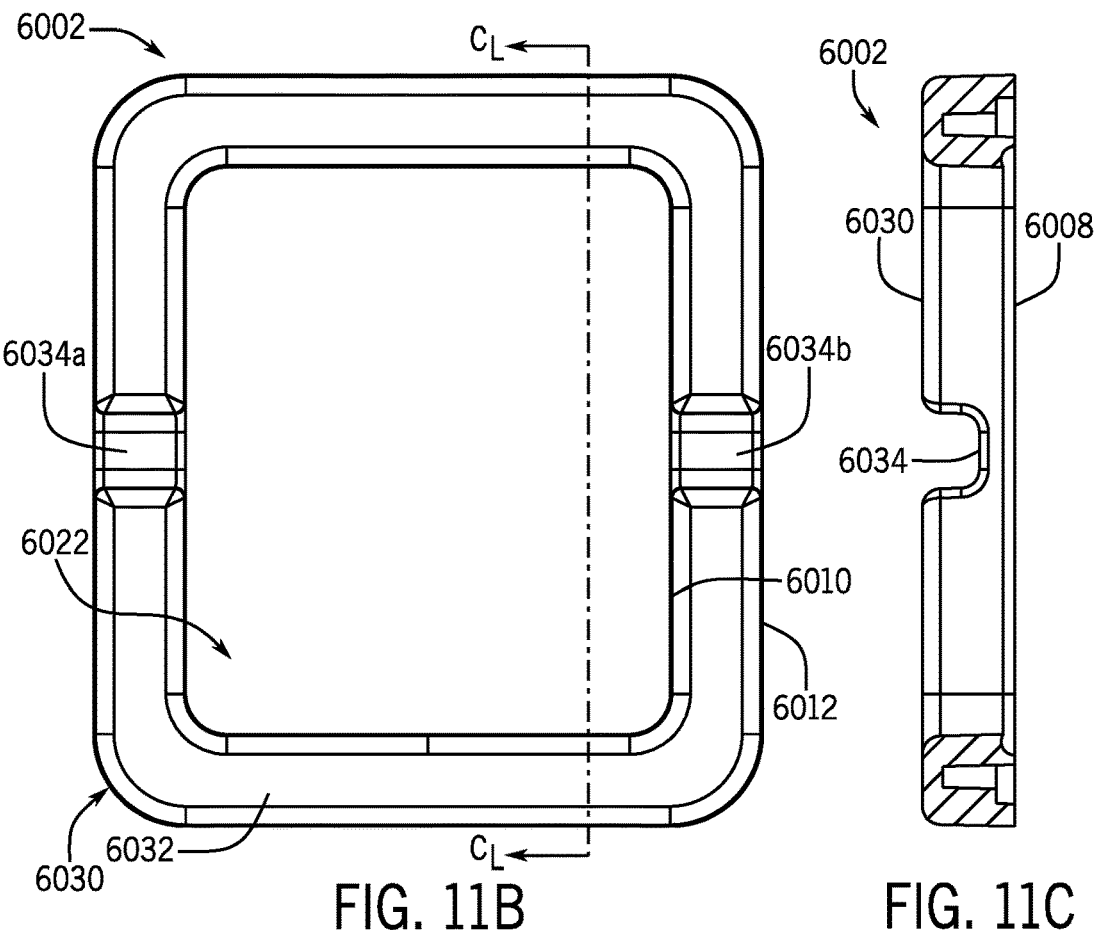
FIG. 11B is a rear view of the gasket case bottom of FIG. 11A, in accordance with some implementations of the present disclosure.
FIG. 11C is a side view of the gasket case bottom of FIG. 11A, in accordance with some implementations of the present disclosure.

Referring specifically to FIGS. 11A-11C, the gasket case bottom 6002 is shown in greater detail, according to implementations of the present disclosure. As shown, FIG. 11A provides a front view of the gasket case bottom 6002, FIG. 11B provides a rear view, and FIG. 11C provides a side view. In some implementations, the gasket case bottom 6002 can include a distal side 6008 (e.g., that is positioned away from the skin grafting system 3000) and a proximal side 6030 (e.g., that is positioned towards the skin grafting system 3000).

As shown by FIG. 11A, the gasket case bottom 6002 can include an exterior edge 6012 and an internal engagement edge 6010. The engagement edge 6010 can contact the exterior of the tissue stabilizer 2014 on the cartridge 2002. In some implementations, the engagement edge 6010 can be firmly secured against the tissue stabilizer 2014. The gasket case bottom 6002 can further include a retainer surface 6014 which can support the gasket 6004 as part of the gasket assembly 6000. In some implementations, the gasket 6004 can be affixed to the retainer surface 6014 via adhesive, which can prevent the gasket 6004 from repositioning during a skin grafting process. When the gasket 6004 is positioned on the retainer surface 6014, the gasket 6004 can contact the exterior of the tissue stabilizer 2014. According to some implementations, the cartridge 2002 can be inserted into an opening 6022 of the gasket case bottom 6002.

As shown by FIG. 11A, the gasket case bottom 6002 can include raised portions 6016 and recessed portions 6018 disposed between the exterior edge 6012 and a retainer edge 6056. In some implementations, the raised portions 6016 and the recessed portions 6018 can be arranged such that the gasket case top 6006 can be press fit onto the gasket case bottom 6002 and retained. As mentioned above, adhesive can be disposed between the gasket case top 6006 and the gasket case bottom 6002, to further retain the structure of the gasket assembly 6000.

Referring to FIGS. 11B-11C, the proximal side 6030 of the gasket case bottom 6002 and a side view of the gasket case bottom 6002 are shown, respectively. The side view of FIG. 11C corresponds to the cut line (CO shown in FIG. 11B. The proximal side 6030 can include an exterior surface 6032, which can be positioned against the cartridge 2002. As shown, the proximal side 6030 can include notches 6034a, 6034b, which can be recessed with respect to the exterior surface 6032. According to some implementations, the notches 6034a, 6034b can be sized to accommodate the extended position of cartridge arms 2020 (see, e.g., FIG. 1, FIG. 5B).

Figure 12A:
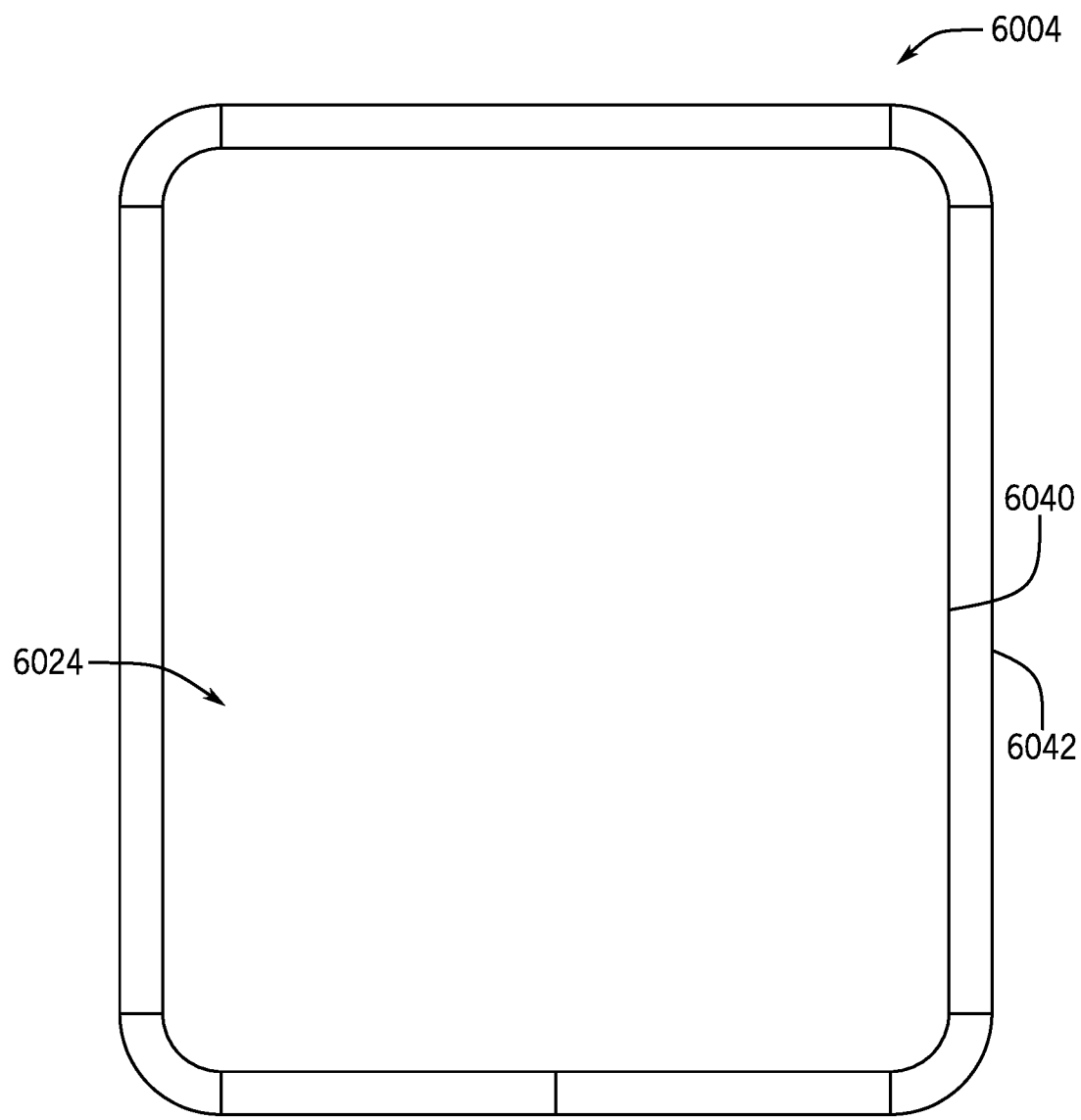
FIG. 12A is a front view of a gasket, in accordance with some implementations of the present disclosure.
Figure 12B:
FIG. 12B is a side view of the gasket of FIG. 12A, in accordance with some implementations of the present disclosure.

Referring now to FIGS. 12A-12B, the gasket 6004 is shown, according to implementations of the present disclosure. In particular, FIG. 12A is a front view of the gasket 6004, and FIG. 12B is a side view of the gasket 6004. The gasket 6004 can be sized to fit on the retainer surface 6014 of the gasket case bottom 6002, and adhesive may be used to prevent movement of the gasket 6004 on the retainer surface 6014. As shown by FIG. 12A, the gasket 6004 can include an engagement edge 6040 and an exterior edge 6042. The engagement edge 6040 can contact the cartridge 2002.

According to some implementations, the gasket 6004 can be formed from silicone or a different hydrophobic material, which can act as a barrier. The cartridge 2002 can be inserted into a gasket opening 6024, which can press the gasket 6004 against the exterior of the cartridge 2002 (e.g., the tissue stabilizer 2014). Accordingly, the gasket 6004 can form a seal with the cartridge 2002 that can prevent clinical soil from entering the handheld device 1000 during a skin grafting process.

Figure 13B:
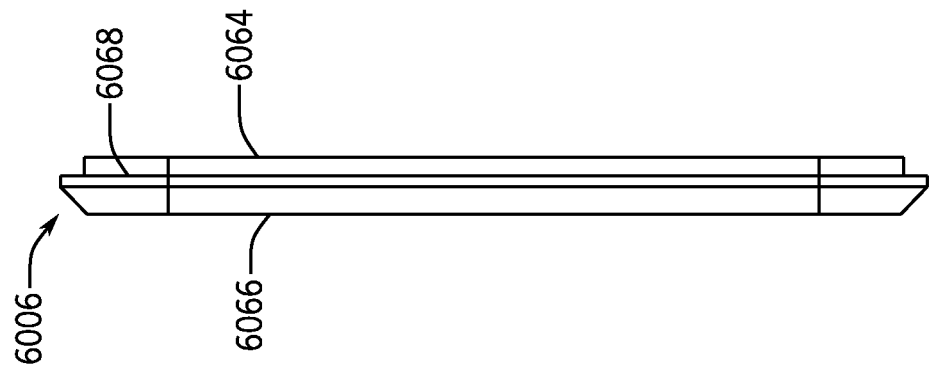
FIG. 13B is a side view of the gasket case top of FIG. 13A, in accordance with some implementations of the present disclosure.
Figure 13A:
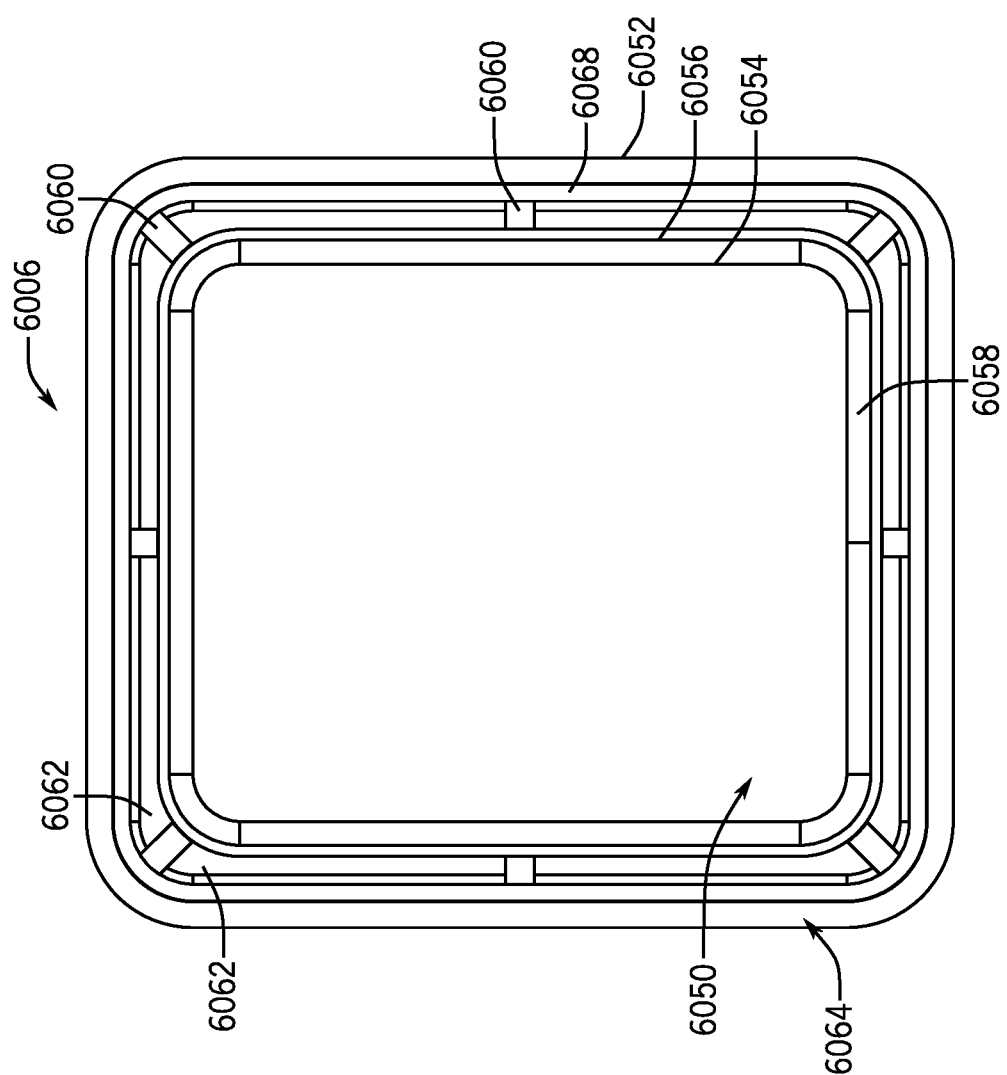
FIG. 13A is a rear view of a gasket case top corresponding to a gasket enclosure, in accordance with some implementations of the present disclosure.

Referring now to FIGS. 13A-13B, the gasket case top 6006 is shown, according to implementations of the present disclosure. In particular, FIG. 13A is a rear view of the gasket case top 6006, and FIG. 13B is a side view of the gasket case top 6006. In some implementations, the gasket case top 6006 can include a distal side 6066 (e.g., that is positioned away from the skin grafting system 3000) and a proximal side 6064 (e.g., that is positioned towards the skin grafting system 3000).

As shown by FIG. 13A, the gasket case top 6006 can include an exterior edge 6052 and an internal engagement edge 6054. In some implementations, the exterior edge 6052 can be aligned with the exterior edge 6012 (corresponding to the gasket case bottom 6002), and the internal engagement edge 6054 can be aligned with the internal engagement edge 6010 (corresponding to the gasket case bottom 6002), with respect to the gasket assembly 6000. The engagement edge 6054 can contact the exterior of the tissue stabilizer 2014 on the cartridge 2002. In some implementations, the engagement edge 6054 can be firmly secured against the tissue stabilizer 2014. The gasket case top 6006 can further include a retainer surface 6058 which can support the gasket 6004 as part of the gasket assembly 6000. In some implementations, the gasket 6004 can be affixed to the retainer surface 6058 (similar to the retainer surface 6014 of the gasket case bottom 6002) via adhesive, which can prevent the gasket 6004 from repositioning during a skin grafting process. When the gasket 6004 is positioned on the retainer surface 6058, the gasket 6004 can contact the exterior of the tissue stabilizer 2014. According to some implementations, the cartridge 2002 can be inserted into an opening 6050 of the gasket case top 6006.

As shown by FIG. 13A, the gasket case top 6006 can include raised portions 6062 and recessed portions 6060 disposed between the exterior edge 6052 and a retainer edge 6056. In some implementations, the raised portions 6062 and the recessed portions 6060 can be arranged such that the gasket case top 6006 can be press fit onto the gasket case bottom 6002 and retained. In some implementations, for example, the raised portions 6062 of the gasket case top 6006 may be complementary (e.g., aligned, similarly sized) to the recessed portions 6018 of the gasket case bottom 6002. Similarly, the recessed portions 6060 of the gasket case top 6006 may be complementary (e.g., aligned, similarly sized) to the raised portions 6016 of the gasket case bottom 6002. As described above, adhesive can be disposed between the gasket case top 6006 and the gasket case bottom 6002, to further retain the structure of the gasket assembly 6000. In some implementations, the gasket case top 6006 can include an engagement surface 6068 protruding from the proximal side 6064. The engagement surface 6068 can be configured to insert into the gasket case bottom 6002, which can help to maintain the overall structure of the gasket assembly 6000.

In some implementations, the gasket case top 6006 and/or the gasket case bottom 6002 can be affixed to a perimeter of the cartridge opening 5002 (i.e., corresponding to the device cover 5000). Further, a portion of the device cover 5000 adjacent to the cartridge opening 5002 can be pressed between the gasket case top 6006 and the gasket case bottom 6002, such that the gasket assembly 6000 is affixed to the perimeter. In some implementations, the gasket case top 6006 can be fastened to an exterior portion of the device cover 5000 using adhesive. Similarly, the gasket case bottom 6002 can be fastened to an interior of the device cover 5000 using adhesive. As described above, adhesive can be further used to couple the gasket case top 6006 to the gasket case bottom 6002. Accordingly, the gasket 6004 can be positioned and retained between the gasket case bottom 6002 and the gasket case top 6006, such that contact between the gasket 6004 and the cartridge 2002 is maintained during a skin grafting process. Accordingly, the gasket assembly 6000 and the device cover 5000 can inhibit fluid ingress (e.g., clinical soil) into the interior volume 5006 of the device cover during a skin grafting process. This can preserve the ability for a user to reuse the handheld device 1000 without performing a potentially lengthy sterilization process of the interior components.

Referring generally to FIGS. 14A-14E, another cincture (e.g., a gasket assembly 7000) is shown, according to implementations of the present disclosure. The gasket assembly can prevent clinical soil from contacting the handheld device by way of the cartridge opening 5002. According to some implementations, the gasket assembly 7000 can be a substantially unitary (e.g., manufactured as a singular component). Alternatively, the gasket assembly 7000 may include portions that are removably affixed. In some implementations, the gasket assembly 7000 can be formed as part of the cartridge 2002 (i.e., manufactured as a singular component). Additionally, in some implementations, the device cover 5000 can be secured directly to the cartridge 2002 (e.g., via adhesive, welding, etc.), thus forming a singular component.

Figure 14B:
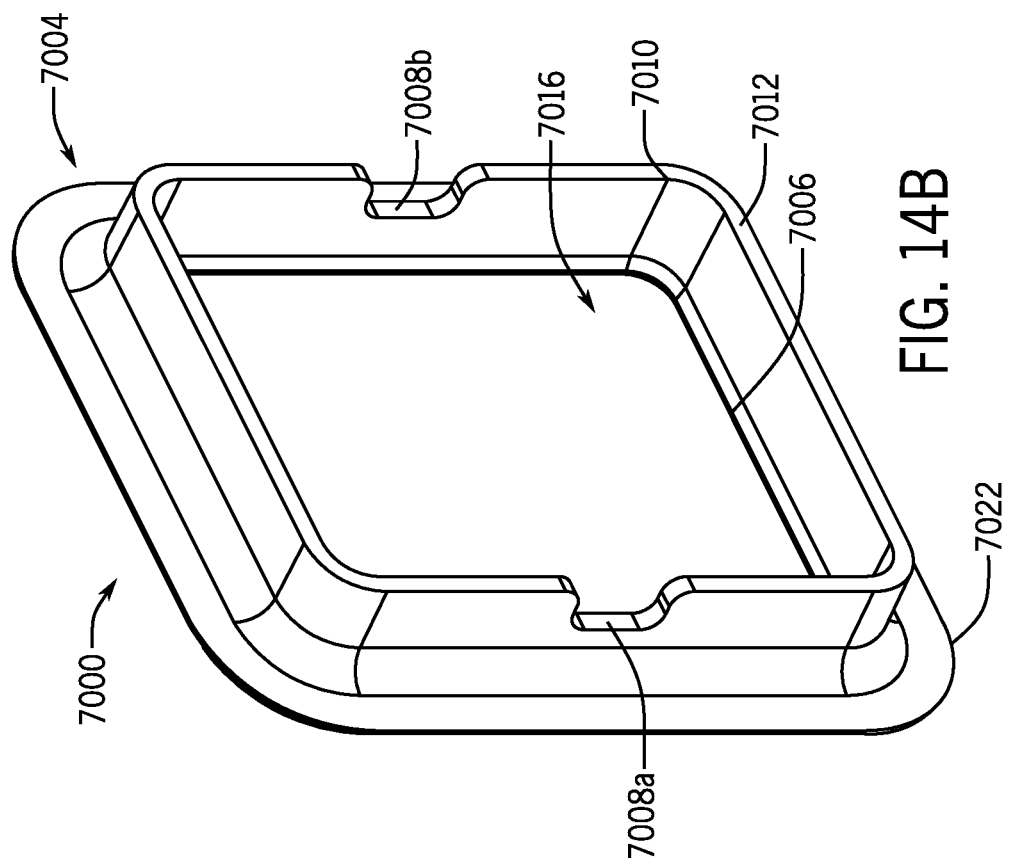
FIG. 14B is a rear perspective view of the gasket of FIG. 14A, in accordance with some implementations of the present disclosure.
Figure 14A:
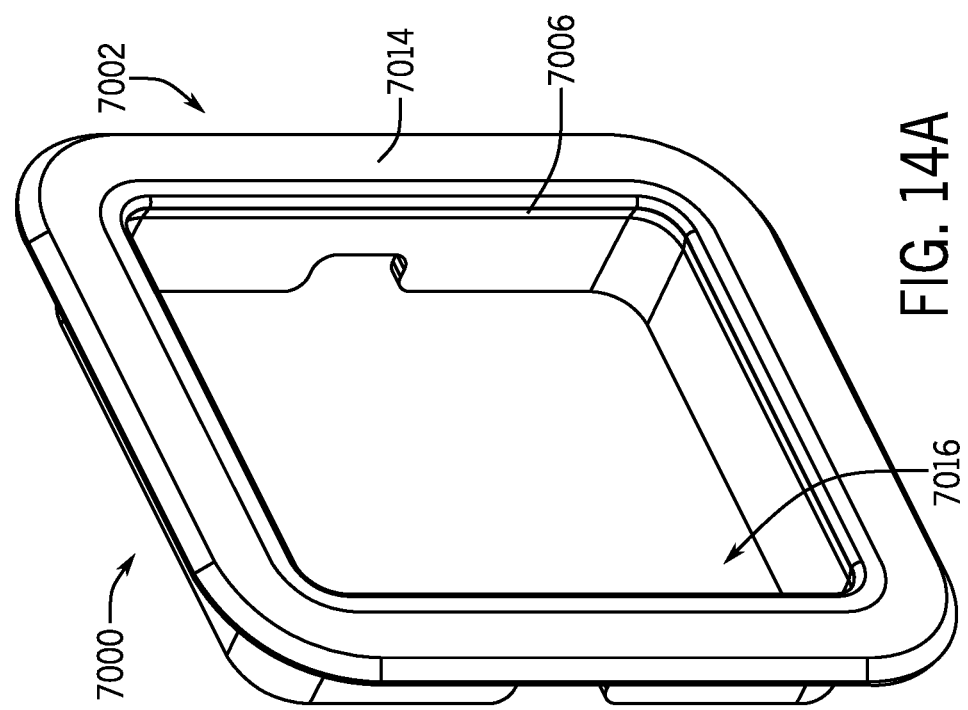
FIG. 14A is a front perspective view of a gasket, in accordance with other implementations of the present disclosure.
Figure 14C:
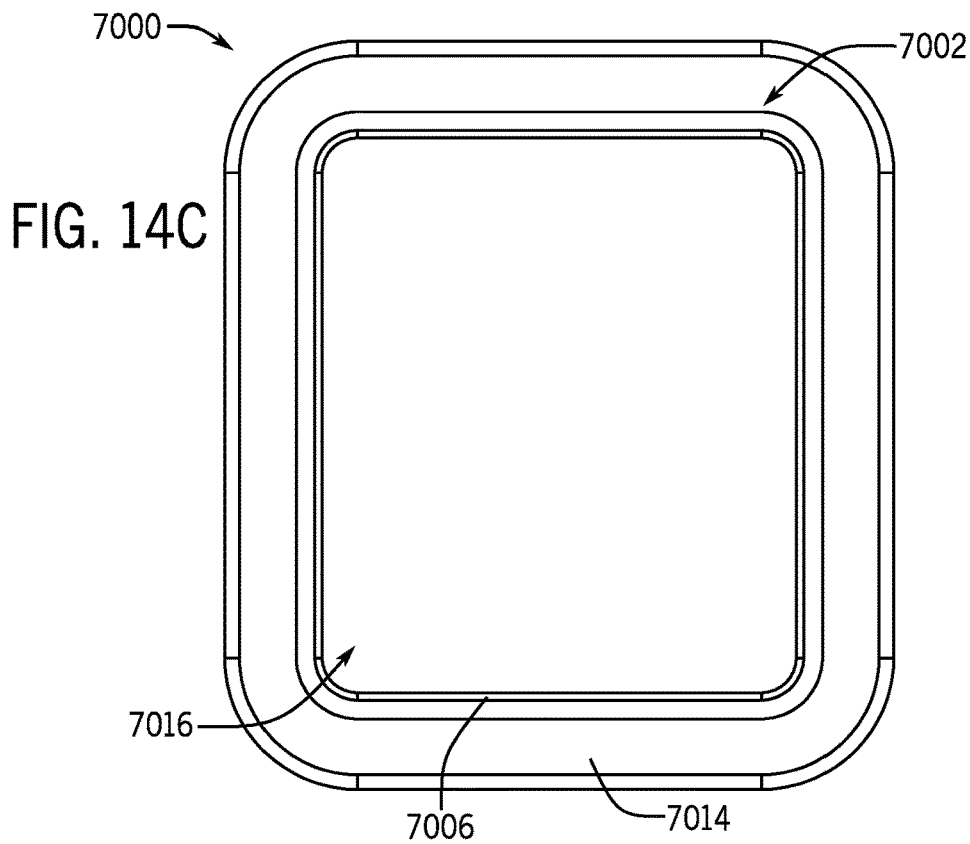
FIG. 14C is a front view of the gasket of FIG. 14A, in accordance with some implementations of the present disclosure.
Figures 14D, 14E:
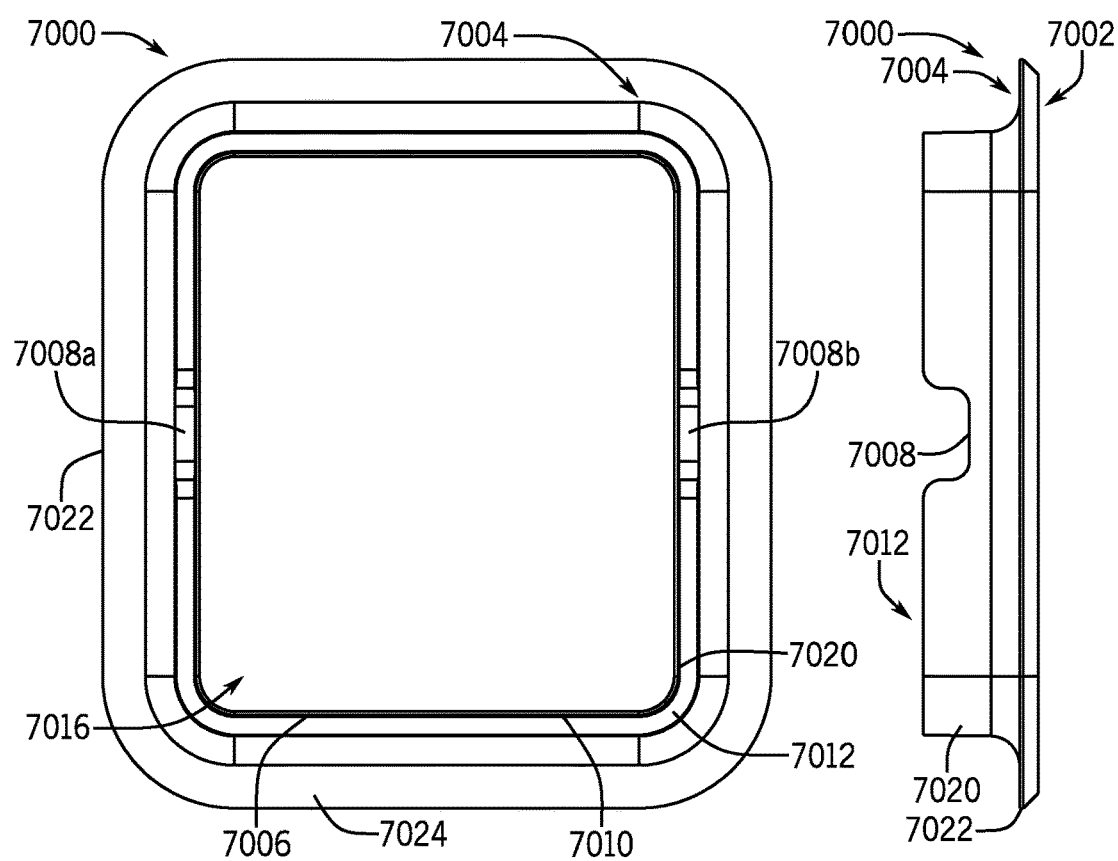
FIG. 14D is a rear view of the gasket of FIG. 14A, in accordance with some implementations of the present disclosure.
FIG. 14E is a side view of the gasket of FIG. 14A, in accordance with some implementations of the present disclosure.

FIG. 14A is a front perspective view of the gasket assembly 7000, in accordance with some implementations. Conversely, FIG. 14B is a rear perspective view of the gasket assembly 7000 of FIG. 14A. In some implementations, the gasket assembly 7000 can include a distal side 7002 (e.g., that is positioned away from the skin grafting system 3000) and a proximal side 7004 (e.g., that is positioned towards the skin grafting system 3000). FIG. 14C is a front view of the gasket assembly 7000, which shows the distal side 7002 in greater detail, including front surface 7014. Similarly, FIG. 14D is a rear view of the gasket assembly 7000, which shows the proximal side 7004 in greater detail, including rear surface 7024. FIG. 14E includes a side view of the gasket assembly 7000.

As shown, the gasket assembly 7000 can include an exterior edge 7022 and an internal engagement edge, which can correspond to a gasket 7006. The cartridge 2002 can be inserted into the opening 7016, which can press the gasket 7006 against the exterior of the cartridge 2002 (e.g., the tissue stabilizer 2014). Accordingly, the gasket 7006 can form a seal with the cartridge 2002 that can prevent clinical soil from entering the handheld device 1000 during a skin grafting process. According to some implementations, the gasket 7006 can be formed from silicone, or a different flexible and/or hydrophobic material.

The gasket assembly 7000 is shown to include a projection 7012, which can include an interior edge 7010 and an exterior edge 7020. The projection 7012 can help to secure the cartridge 2002, upon insertion into opening 7016. The projection 7012 can contact the cartridge 2002 via the interior edge 7010 and a proximal edge, according to some implementations. Referring particularly to FIGS. 14B, 14D, and 14E, the proximal side 7004 is shown to include notches 7008a, 7008b, which can be recessed with respect to the projection 7012. As shown, the notches 7008a, 7008b can be sized to accommodate the extended position of cartridge arms 2020 (see, e.g., FIG. 1, FIG. 5B).

According to some implementations, the front surface 7014 can be positioned exterior to the device cover 5000. The gasket assembly 7000 can be affixed to a perimeter of the cartridge opening 5002 (i.e., corresponding to the device cover 5000). In some implementations, the gasket assembly 7000 can be fastened to an exterior portion of the device cover 5000 using adhesive. As an example, the rear surface 7024 of the gasket assembly 7000 (see, e.g., FIG. 14D) can adhere to the exterior portion of the device cover. In other implementations, the gasket assembly 7000 can be affixed to the device cover 5000 using alternative methods.

As described above, the cincture (e.g., the gasket assembly 7000), and the device cover 5000 can inhibit fluid ingress (e.g., clinical soil) into the interior volume 5006 of the device cover during a skin grafting process. This can preserve the ability for a user to reuse the handheld device 1000 without performing a potentially lengthy sterilization process of the interior components.

Figure 15A:
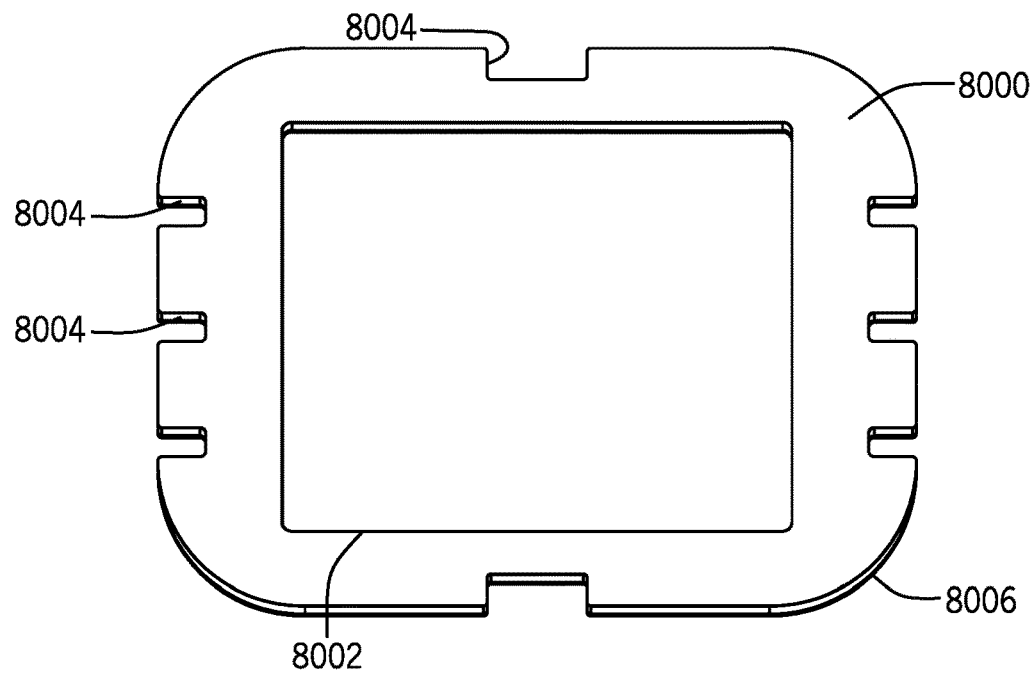
FIG. 15A is a top view of an absorptive material corresponding to a clinical soil control system, in accordance with some implementations of the present disclosure.
Figure 15B:
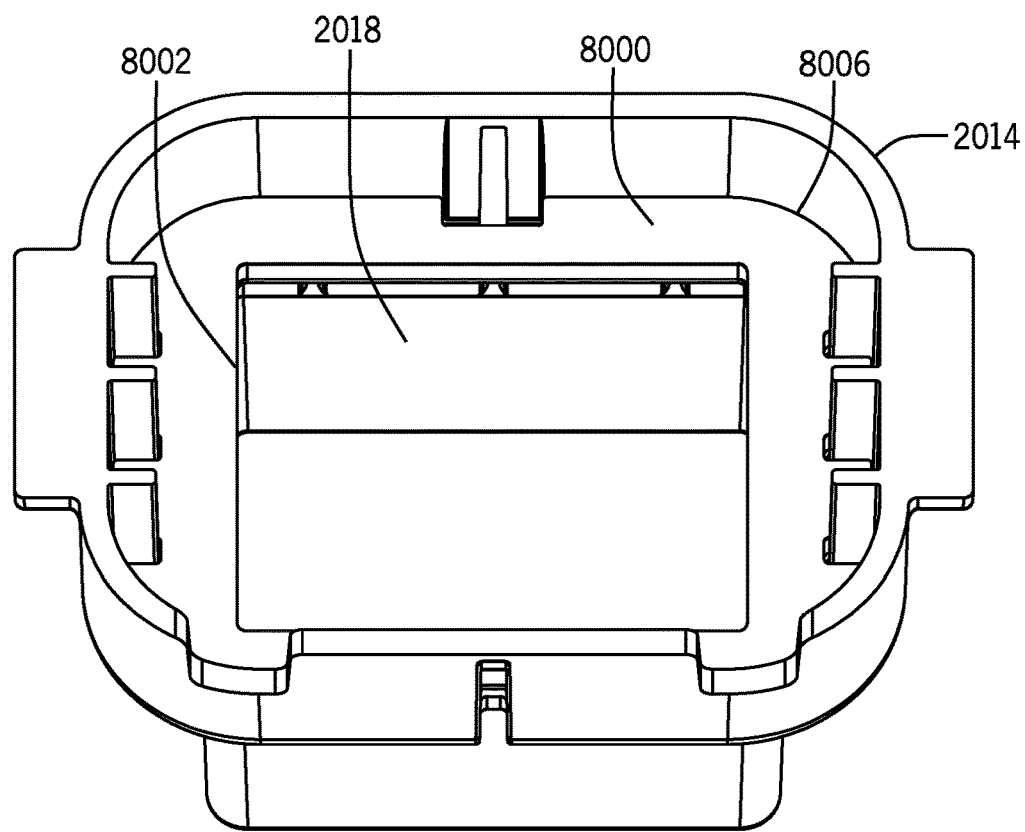
FIG. 15B is a top view of the absorptive material of FIG. 15A, as positioned within a tissue stabilizer, in accordance with some implementations of the present disclosure.
Figure 15C:
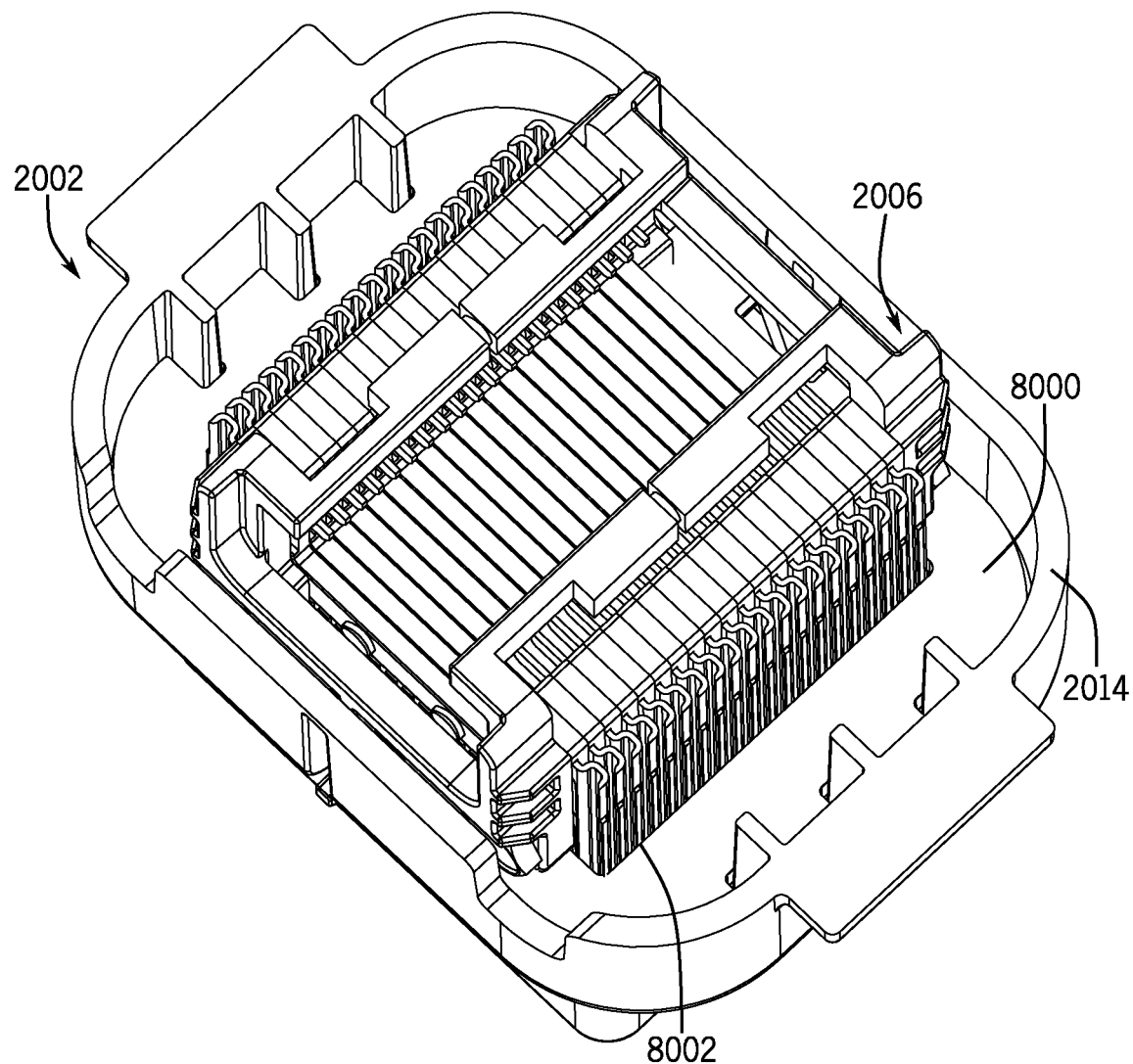
FIG. 15C is a perspective view of the absorptive material of FIG. 15A, as positioned around a microneedle array, in accordance with some implementations of the present disclosure.

Referring now to FIGS. 15A-15C, an absorptive material 8000 is shown, in accordance with implementations of the present disclosure. Specifically, FIG. 15A is a top view of the absorptive material 8000 corresponding to a clinical soil control system, FIG. 15B is a top view of the absorptive material 8000 as positioned within the tissue stabilizer 2014, and FIG. 15C is a perspective view of the absorptive material 8000 as positioned around the microneedle array 2006. Notably, in some implementations, a repellant material (e.g., a hydrophobic material) may be used instead of the absorptive material 8000. The repellant material can act as a barrier around the microneedle array 2006, thus diverting clinical soil away from the interior of the handheld device 1000.

In some implementations, the absorptive material 8000 can inhibit fluid ingress (e.g., from clinical soil) into the interior of the handheld device 1000 via the cartridge 2002. The absorptive material 8000 can include polyacrylate fibers, which can absorb and retain fluids (e.g., fluids from a skin grafting process). Additionally, in some implementations, the absorptive material 8000 can include hydrophilic fibers which can wick and retain fluids. As an example, the absorptive material 8000 may have substantially similar properties to Qwick™, an absorbent wound dressing commercially available from Medline Industries, Inc.

In some implementations, the absorptive material 8000 can include multiple layers. As an example, a first layer can be a hydrophilic layer such as 100% TENCEL™, or a hydrophilic equivalent. A second layer, as an example, can be a super absorbent polymer. As used herein, a super absorbent polymer (SAP) is a material that can absorb and retain an extremely large amount of a liquid relative to its own mass. A third layer can be a polypropylene fiber, as an example. In some implementations, additional layers, or fewer layers may be included in the absorptive material 8000.

As shown by FIGS. 15A-15C, the absorptive material 8000 can be cut to complement the size and shape of the tissue stabilizer 2014 and the microneedle chamber 2018. In some implementations, the absorptive material 8000 can include an interior edge 8002 and an exterior edge 8006. The interior edge 8002 can be positioned to be substantially aligned with an opening of the tissue stabilizer 2014 (e.g., an edge of the microneedle chamber 2018). The exterior edge 8006 can be positioned against an interior wall of the tissue stabilizer 2014. In some implementations, the absorptive material 8000 can be secured to an interior surface of the tissue stabilizer 2014 using adhesive. The adhesive can prevent movement of the absorptive material 8000 during a skin grafting process. As an example, securing the absorptive material 8000 within the tissue stabilizer 2014 can prevent the absorptive material 8000 from interfering with the movement of the microneedles 2050 during harvesting and/or scattering. In some implementations, adhesive can be in the form of a liquid or a film. Additionally, the absorptive material 8000 can be secured to an interior surface of the tissue stabilizer 2014 via various welding methods, such as RF welding. Other, for example, mechanical methods of securing the absorptive material 8000 to the tissue stabilizer 2014 may be used.

The absorptive material 8000 can include various cutouts 8004 to accommodate the features of the tissue stabilizer 2014. In particular, cutouts 8004 can be positioned to provide clearance for the cartridge arms 2020 (as shown and described with respect to FIGS. 1 and 5B). Notably, the interior edge 8002 of the absorptive material 8000 can be flush with the edge of the microneedle chamber 2018, so that fluid originating from the microneedles 2050 can be wicked away and retained by the absorptive material 8000. Accordingly, the absorptive material 8000 can inhibit fluid ingress (e.g., clinical soil) into the interior of the handheld device 1000 during a skin grafting process.

As described above, a clinical soil control system, according to some implementations of the present disclosure, can include the device cover 5000, the cincture (e.g., gasket assembly 6000, 7000), and the absorptive material 8000. In some configurations, the clinical soil control system can include one of, or various combinations of: the device cover 5000, the cincture (gasket assembly 6000, 7000), and the absorptive material 8000.

FIGS. 16A-16E illustrate a clinical soil control system without a gasket assembly. The clinical soil control system includes a cincture (e.g., device cover 9000). The device cover 9000 includes a cartridge opening 9002 and an access opening 9003, and can cover a portion of, or the entirety of, the handheld device 1000. The access opening 9003 can be sized to receive the handheld device 1000 into an interior volume 9006 of the device cover 9000 and, also, to allow the user to hold and interact with the corresponding elements of the handheld device 1000. As one example, the interior volume 9006 can accommodate the opening and closing of the loading door 1004, which can begin the initialization process described above. The device cover 9000 can include an elastic band and any other similar features as described with respect to device cover 5000.

In some implementations, the cartridge opening 9002 is sized and shaped to receive the cartridge 2002. In particular, the cartridge opening 9002 can receive the peripheral housing 2017 formed by the tissue stabilizer 2014. The cartridge opening 9002 can include a projection 9004, which forms the cartridge opening 9002. The projection 9004 can extend away from the interior volume 9006 of the device cover 9000 to a length that is shorter, the same, or longer than the length that the peripheral housing 2017 extends away from the body of the cartridge 2002. The projection 9004 has an interior surface 9010 that extends around the inner periphery of the projection 9004. According to some implementations, the projection 9004 can be made from the same or similar material as the body of the device cover 9000.

The cartridge opening 9002 can be a size and/or shape that complements the size and shape of the peripheral housing 2017. For example, if the peripheral housing 2017 forms a quadrangular prism as shown in FIGS. 16A-16E, the interior surface 9010 and cartridge opening 9002 can be shaped to contact the exterior surface of a substantially similar quadrangular prism. The peripheral housing 2017, the cartridge opening 9002, and the interior surface 9010 of the projection 9004 can also be formed as other complementary shape combinations, e.g., cone, cuboid, triangular prism, and the like. When the cartridge 2002 is inserted into the cartridge opening 9002, the interior surface 9010 can contact the peripheral housing 2017 to form a seal that prevents the ingress of fluid past the tissue stabilizer 2014 into the housing 1036. In some implementations, the cartridge opening 9002 and/or the dimensions of the interior surface 9010 are undersized in comparison to the dimensions of the peripheral housing 2017. In this instance, the device cover 9000 can be stretched over the cartridge 2002 to create a tight seal that prevents fluid ingress. Accordingly, the device cover 9000 is a cincture, via the cartridge opening 9002, even absent a gasket assembly.

Figure 16B:
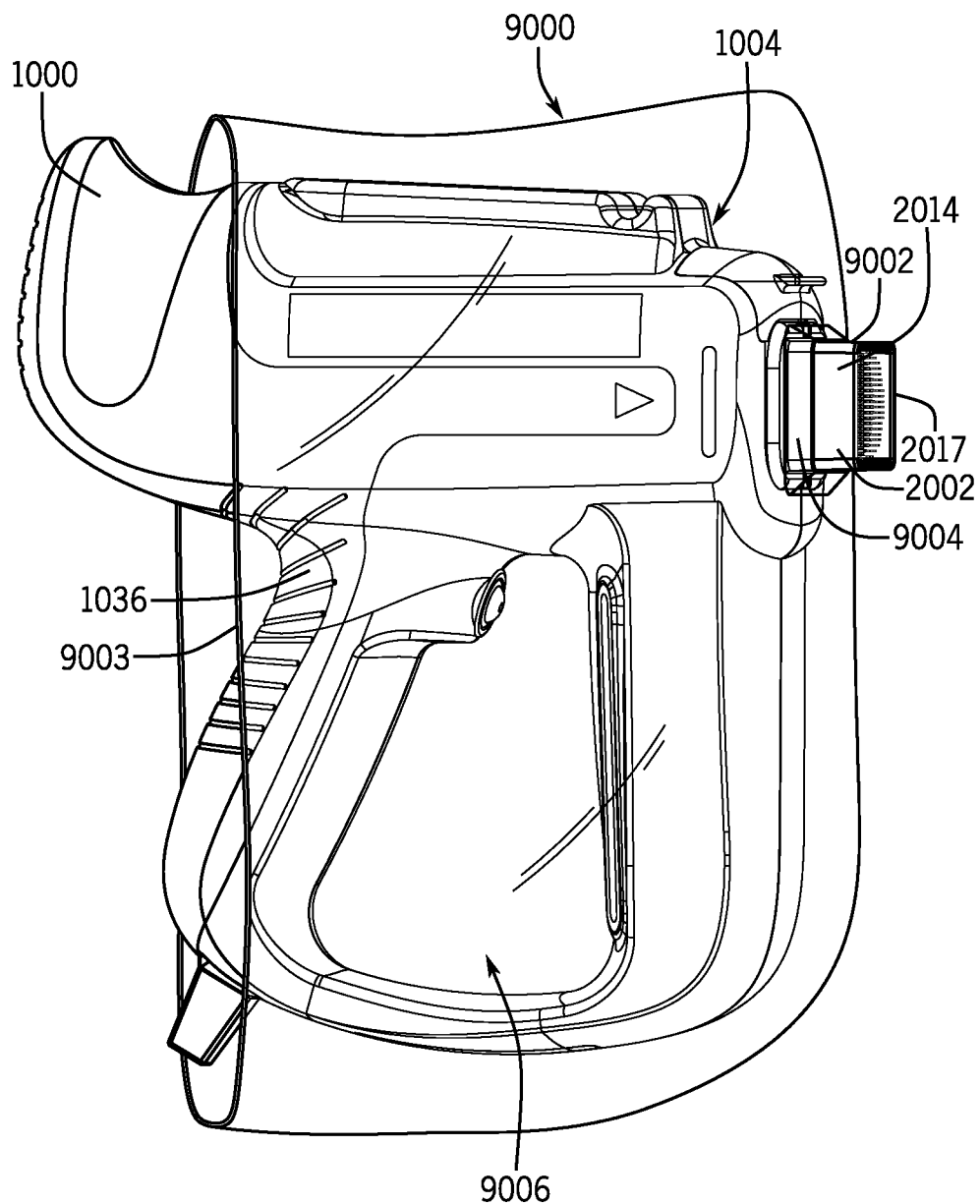
FIG. 16B is a side view of the applied clinical soil control system of FIG. 16A, in accordance with some implementations of the present disclosure.
Figure 16C:
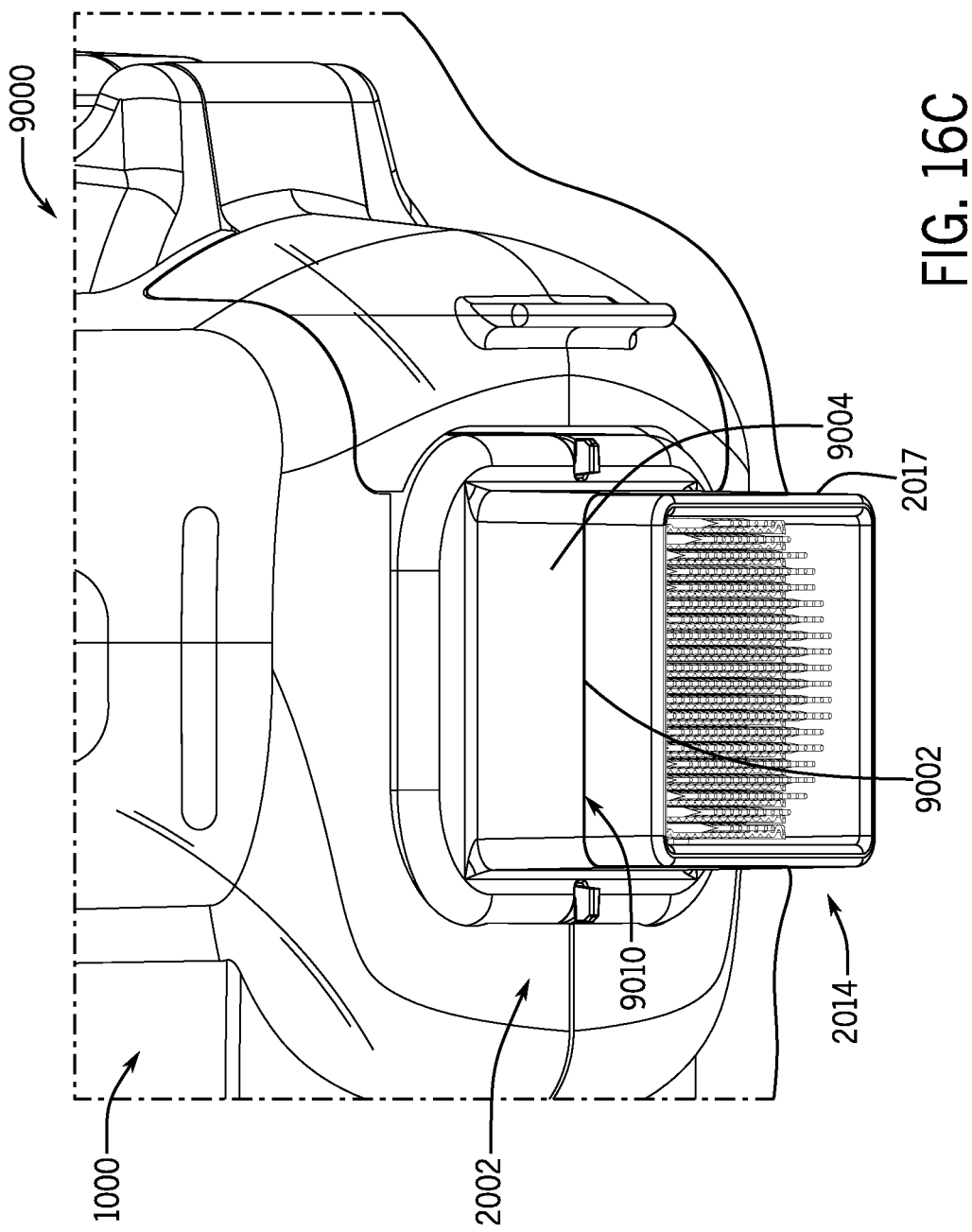
FIG. 16C is a front perspective view of the applied clinical soil control system of FIG. 16A, in accordance with some implementations of the present disclosure.
Figure 16D:
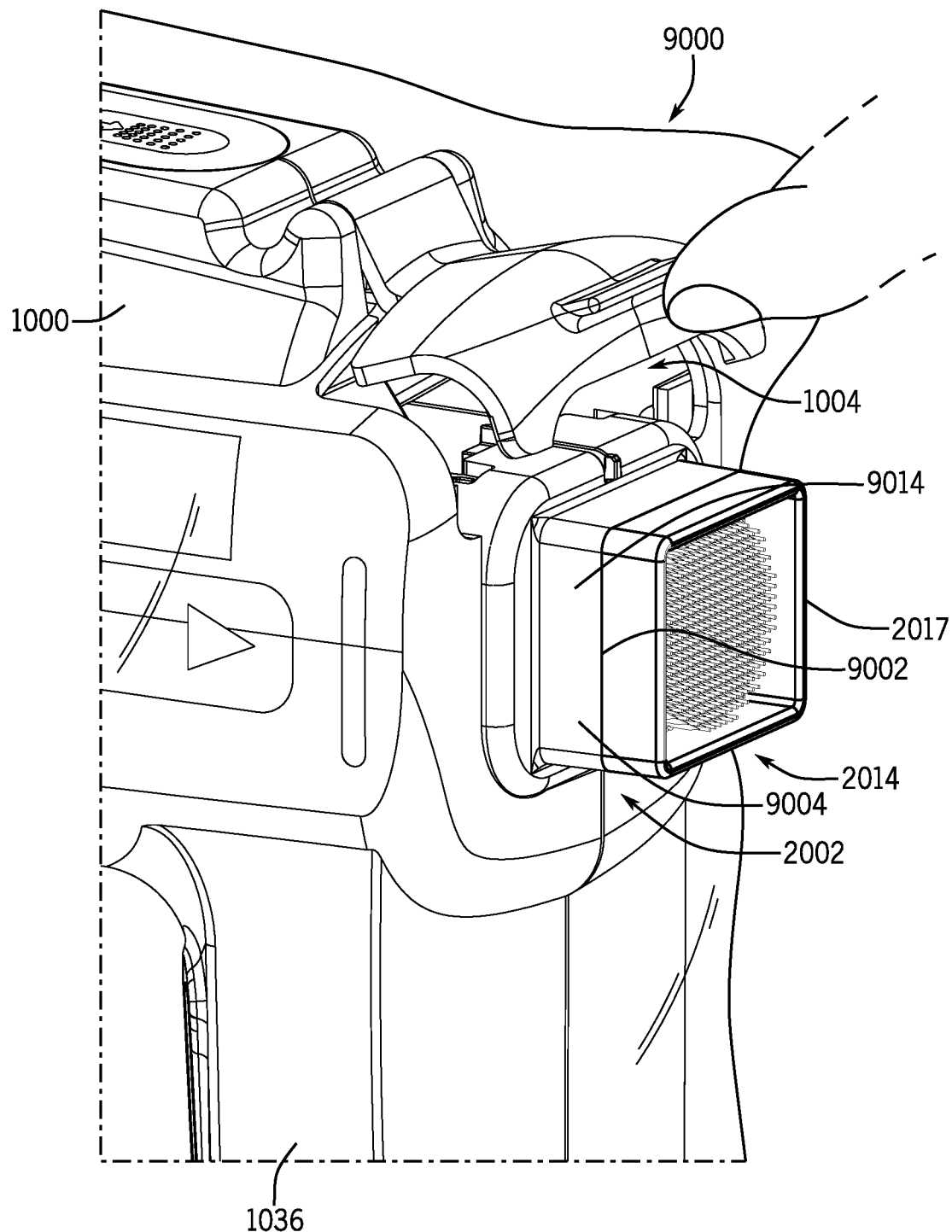
FIG. 16D is a side perspective view of the applied clinical soil control system of FIG. 16A, in accordance with some implementations of the present disclosure.
Figure 16E:
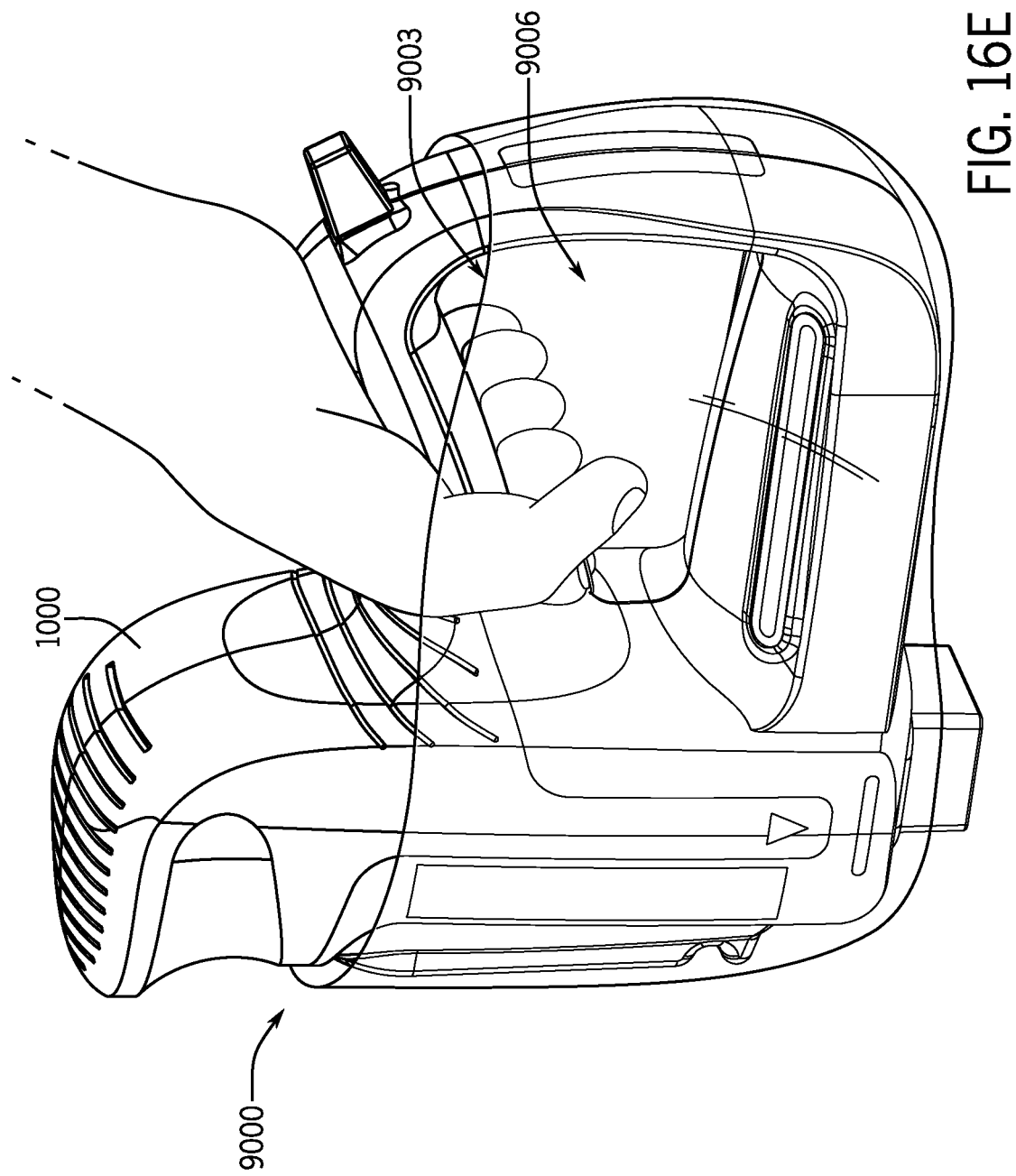
FIG. 16E is a perspective view of a user engaging with the applied clinical soil control system of FIG. 16A, in accordance with some implementations of the present disclosure.

In some implementations, the projection 9004 can include an elastic loop 9014 to securely, but removably, attach the projection 9004 to the cartridge 2002 (see, e.g., FIG. 16D). The elastic loop 9014 can be integral with, or separately attached to, the outside of projection 9004 anywhere along the length of the projection 9004 that contacts the cartridge 2002. In some implementations, the interior surface 9010 can include an elastomeric strip that creates a seal between the projection 9004 and the cartridge 2002. Additionally, in some implementations the interior surface 9010 can include adhesive. The absorptive material 8000 (as described above) can be positioned on the interior surface 9010, within the tissue stabilizer 2014, or positioned in both locations. Various combinations of the above features can be used to modify or improve the seal created between the device cover 9000 and the cartridge 2002.

The clinical soil control system can prevent fluid ingress into the handheld device 1000 (e.g., via the housing 1036), and/or general fluid exposure to the reusable handheld device 1000 (e.g., the exterior of the housing 1036). This can preserve the ability for a user to reuse the handheld device 1000 without performing a potentially lengthy sterilization process of the interior components.

While the present disclosure may be susceptible to various modifications and alternative forms, specific configurations have been shown by way of example in the drawings and have been described in detail herein. However, it should be understood that the present disclosure is not intended to be limited to the particular forms disclosed. Rather, the present disclosure is to cover all modifications, equivalents, and alternatives falling within the spirit and scope of the present disclosure as defined by the following appended claims.

This written description uses examples to disclose the present disclosure, including the best mode, and also to enable any person skilled in the art to practice the present disclosure, including making and using any devices or systems and performing any incorporated methods. The patentable scope of the present disclosure is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Finally, it is expressly contemplated that any of the processes or steps described herein may be combined, eliminated, or reordered. Accordingly, this description is meant to be taken only by way of example, and not to otherwise limit the scope of this present disclosure.

The invention claimed is:

1. A skin grafting system comprising: a handheld device comprising a device housing forming an interior that secures a drive system; a cartridge comprising a plurality of hollow microneedles surrounded by a peripheral housing and configured to be operated by the handheld device to extend and retract during a skin grafting process; an absorptive material disposed within the peripheral housing and surrounding the plurality of hollow microneedles; a device cover formed of a flexible polymer sheet defining an interior volume for the handheld device, and including at least a first opening configured to receive the cartridge; and a cincture comprising: a gasket configured to be affixed to a perimeter of the first opening of the device cover and to secure the device cover about the first opening to at least one of the handheld device or the cartridge to inhibit fluid ingress into the interior volume of the device cover, and wherein the absorptive material is configured to inhibit fluid ingress into the interior of the handheld device via the cartridge, wherein the gasket is configured to surround the peripheral housing of the cartridge.

2. The skin grafting system of claim 1, wherein the absorptive material is secured to an interior surface of the peripheral housing using adhesive.

3. The skin grafting system of claim 1, wherein the absorptive material is positioned within the peripheral housing such that an interior edge of the absorptive material is substantially aligned with an opening of the peripheral housing.

4. The skin grafting system of claim 1, wherein the absorptive material comprises polyacrylate fibers configured to absorb and retain fluids resulting from the skin grafting process.

5. The skin grafting system of claim 1, wherein the absorptive material comprises hydrophilic fibers configured to wick and retain fluids resulting from the skin grafting process.

6. The skin grafting system of claim 1, wherein the absorptive material comprises a plurality of layers, including a first layer comprising a hydrophilic material, and a second layer comprising a super absorbent polymer.

7. The skin grafting system of claim 6, wherein the plurality of layers further comprises a third layer comprising polypropylene fiber.

8. The skin grafting system of claim 1, wherein the flexible polymer sheet is comprised of thermoplastic polyurethane having a thickness within the range 0.1 mm to 2.0 mm, inclusive.

9. A skin grafting system comprising: a handheld device comprising a device housing forming an interior that secures a drive system; a cartridge comprising a plurality of hollow microneedles surrounded by a peripheral housing and configured to be operated by the drive system to extend and retract during a skin grafting process; a device cover formed of a flexible polymer sheet defining an interior volume for the handheld device, and including at least a first opening configured to receive the cartridge; and a cincture comprising: a gasket configured to be affixed to a perimeter of the first opening of the device cover and to secure the device cover about the first opening to the cartridge to inhibit fluid ingress into the interior volume of the device cover, wherein the gasket is configured to surround the peripheral housing of the cartridge.

10. The skin grafting system of claim 9, wherein the device cover further includes a second opening, the second opening configured to receive the handheld device into the interior volume and enabling access to the handheld device during the skin grafting process.

11. The skin grafting system of claim 10, wherein the second opening comprises a means for restricting a size of the second opening.

12. The skin grafting system of claim 9, further comprising an absorptive material adhered to an interior of the peripheral housing and configured to inhibit fluid ingress into the interior of the handheld device.

13. The skin grafting system of claim 12, wherein the absorptive material comprises hydrophilic fibers configured to wick away fluids from the plurality of microneedles.

14. The skin grafting system of claim 12, wherein the absorptive material surrounds the plurality of microneedles.

15. The skin grafting system of claim 12, wherein the absorptive material comprises a plurality of layers, including a first layer comprising a hydrophilic material, and a second layer comprising an absorbent polymer.

16. A clinical soil control system comprising: a device cover formed of a flexible polymer sheet defining an interior volume for a skin grafting device and including at least a first opening configured to receive a portion of the skin grafting device; an absorptive material disposed within a peripheral housing of a cartridge and surrounding a plurality of hollow microneedles of the cartridge, and a cincture comprising: a gasket configured to be affixed to a perimeter of the first opening of the device cover and to secure the device cover about the first opening to the skin grafting device to inhibit fluid ingress into the interior volume of the device cover during a skin grafting process performed using the skin grafting device, wherein the gasket is configured to surround the peripheral housing of the cartridge.

17. The clinical soil control system of claim 16, wherein the flexible polymer sheet is comprised of thermoplastic polyurethane.

18. The clinical soil control system of claim 16, wherein the flexible polymer sheet is translucent and white, blue, or yellow.

19. The clinical soil control system of claim 16, wherein the device cover further includes a second opening, the second opening configured to receive the skin grafting device into the interior volume and sized to enable access to the skin grafting device during the skin grafting process.

20. The clinical soil control system of claim 19, wherein the second opening includes an elastic band for restricting a size of the second opening.

* * * * *

UNITED STATES PATENT AND TRADEMARK OFFICE
CERTIFICATE OF CORRECTION

PATENT NO. : 11,633,208 B2
APPLICATION NO. : 16/741535
DATED : April 25, 2023
INVENTOR(S) : Kelly Molinaro et al.

It is certified that error appears in the above-identified patent and that said Letters Patent is hereby corrected as shown below:

In the Specification

Column 23, Line 39, "(CO" should be --($C_L$)--.

Signed and Sealed this
Sixth Day of June, 2023

Katherine Kelly Vidal
*Director of the United States Patent and Trademark Office*